(12) United States Patent
Koike et al.

(10) Patent No.: US 7,534,914 B2
(45) Date of Patent: May 19, 2009

(54) SUBSTITUTED METHYL ARYL OR HETEROARYL AMIDE COMPOUNDS

(75) Inventors: Hiroki Koike, Chita-gun (JP); Kana Kon-i, Chita-gun (JP); Yukari Matsumoto, Chita-gun (JP); Kazunari Nakao, Chita-gun (JP); Yoshiyuki Okumura, Chita-gun (JP); Tatsuya Yamagishi, Chita-gun (JP)

(73) Assignee: ReQualia Pharma Inc., Aichi-ken (JP)

( * ) Notice: Subject to any disclaimer, the term of this patent is extended or adjusted under 35 U.S.C. 154(b) by 624 days.

(21) Appl. No.: 11/118,497

(22) Filed: Apr. 29, 2005

(65) Prior Publication Data

US 2005/0267170 A1     Dec. 1, 2005

Related U.S. Application Data

(60) Provisional application No. 60/568,088, filed on May 4, 2004.

(51) Int. Cl.
*C07C 229/00*     (2006.01)

(52) U.S. Cl. .................................... 562/450

(58) Field of Classification Search ................ 562/450
See application file for complete search history.

(56) References Cited

U.S. PATENT DOCUMENTS

2002/0037875 A1    3/2002   Banville et al.

FOREIGN PATENT DOCUMENTS

| EP | 1229034 B1 | 4/2005 |
| WO | WO 98/23581 | 6/1998 |
| WO | WO 98/45268 A1 | 10/1998 |
| WO | WO 00/20371 A1 | 4/2000 |
| WO | WO 00/71508 A2 | 11/2000 |
| WO | WO 00/71508 A3 | 11/2000 |
| WO | WO 03/016254 A1 | 2/2003 |
| WO | WO 03/030937 A1 | 4/2003 |

OTHER PUBLICATIONS

Jasse, Bruno, w(W-hydroxyamido)carboxylic acids, 1969,Bulletin de la Societe Chimique de France, 3, 953-5, abtract p. 1.*

* cited by examiner

*Primary Examiner*—Taylor Victor Oh
(74) *Attorney, Agent, or Firm*—Scully, Scott, Murphy & Presser, P.C.

(57) ABSTRACT

This invention provides a compound of the formula (I):

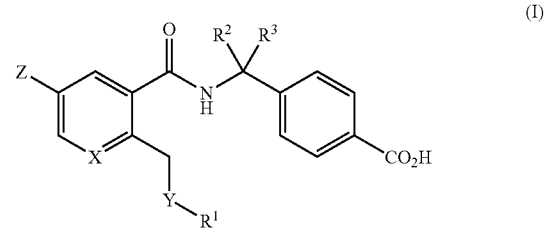

(I)

wherein

X represents a carbon atom or the like: Y represents imino, or the like: $R^1$ represents an alkyl group having from 1 to 6 carbon atoms or the like: $R^2$ and $R^3$ independently represents a hydrogen atom or the like. These compounds are useful for the treatment of disease conditions mediated by prostaglandin such as pain, or the like in mammalian. This invention also provides a pharmaceutical composition comprising the above compound.

12 Claims, No Drawings

SUBSTITUTED METHYL ARYL OR HETEROARYL AMIDE COMPOUNDS

This application is a United States utility application, which claims the benefit of priority to U.S. Provisional Application No. 60/568,088, filed May 4, 2004.

TECHNICAL FIELD

This invention relates to novel substituted methyl aryl or heteroaryl amide compounds. These compounds are useful as antagonists of prostaglandin $E_2$ receptor, and are thus useful for the treatment or alleviation of pain and inflammation and other inflammation-associated disorders. The present invention also relates to a pharmaceutical composition comprising the above compounds.

BACKGROUND ART

Prostaglandins are mediators of pain, fever and other symptoms associated with inflammation. Prostaglandin $E_2$ ($PGE_2$) is the predominant eicosanoid detected in inflammation conditions. In addition, it is also involved in various physiological and/or pathological conditions such as hyperalgesia, uterine contraction, digestive peristalsis, awakeness, suppression of gastric acid secretion, blood pressure, D platelet function, bone metabolism, angiogenesis or the like.

Four $PGE_2$ receptor subtypes ($EP_1$, $EP_2$, $EP_3$ and $EP_4$) displaying different pharmacological 0 properties have been cloned. The $EP_4$ subtype, a Gs-coupled receptor, stimulates cAMP production, and is distributed in a wide variety of tissue suggesting a major role in $PGE_2$-mediated biological events.

WO03/016254 and WO00/20371 describe carboxylic acids compounds as prostaglandin receptor antagonists.

Although substituted methyl benzamide compounds are described in WO03/030937, it relates to mitochondrial benzodiazepine receptor antagonists. Further, WO98/45268 and EP1229034 describe substituted nicotinamide compounds, however they relate to inhibitors of phosphodiesterases 4 isozymes. It would be desirable if there were provided a novel $EP_4$ selective antagonist with potent binding activity by systemic administration, and both with potent $EP_4$ receptor binding activity and with metabolic stability.

BRIEF DISCLOSURE OF THE INVENTION

It has now been found that certain substituted methyl aryl or heteroaryl amide compounds are $EP_4$ receptor selective antagonists with analgesic activity by systemic administration.

The compounds of the present invention may show less toxicity, good absorption, distribution, good solubility, low protein binding affinity, less drug-drug interaction, a reduced inhibitory activity at HERG channel and good metabolic stability. In particular, the compounds of the present invention display improved half-life.

The present invention provides a compound of the following formula (I):

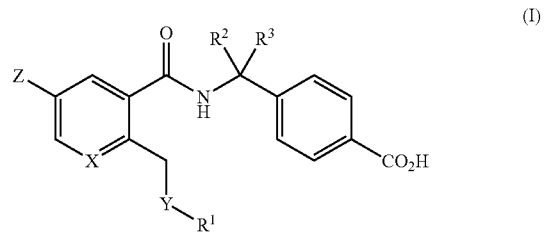

wherein
X represents —CH— or a nitrogen atom;
Y represents —$NR^4$, an oxygen atom or a sulfur atom;
$R^4$ represents a hydrogen atom or an alkyl group having from 1 to 3 carbon atoms;
Z represents a hydrogen atom or a halogen atom;
$R^1$ represents an alkyl group having from 1 to 6 carbon atoms optionally substituted with an alkoxy group having from 1 to 6 carbon atoms or a cycloalkyl group having from 3 to 7 carbon atoms; a cycloalkyl group having from 3 to 7 carbon atoms optionally substituted with an alkyl group having from 1 to 3 carbon atoms; a phenyl group optionally substituted with one or more substituents α; or a group $Het^1$ optionally substituted with one or more substituents α;
$Het^1$ represents a heterocyclic group having from 4 to 7 ring atoms which contains either from 1 to 4 ring nitrogen heteroatoms or from 0 to 2 nitrogen ring heteroatoms and 1 oxygen or 1 sulfur ring heteroatom;
$R^2$ and $R^3$ independently represent a hydrogen atom or an alkyl group having from 1 to 3 carbon atoms; or
$R^2$ and $R^3$ groups together form an alkylene chain having from 3 to 6 carbon atoms; and
said substituent α is selected from the group consisting of halogen atoms, alkyl groups having from 1 to 4 carbon atoms, haloalkyl groups having from 1 to 4 carbon atoms, hydroxy groups, alkoxy groups having from 1 to 4 carbon atoms, haloalkoxy groups having from 1 to 4 carbon atoms, cyano groups, hydroxy alkyl groups having from 1 to 4 carbon atoms, alkoxyalkyl groups having from 1 to 4 carbon atoms in alkoxy and alky groups, alkylsulfonyl groups having from 1 to 4 carbon atoms, alkanoyl groups having from 2 to 5 carbon atoms, alkenyl groups having from 2 to 4 carbon atoms, alkynyl groups having from 2 to 4 carbon atoms, alkylthio groups having from 1 to 4 carbon atoms, nitro groups, amino groups, mono- or di-alkylamino groups having from 1 to 4 carbon atoms, aminosulfonyl groups, alkoxycarbonyl groups having from 1 to 4 carbon atoms, alkylsufonylamino groups having from 1 to 4 carbon atoms, cycloalkyl groups having from 3 to 7 carbon atoms and a mono- or di-alkylaminocarbonyl groups having from 1 to 6 carbon atoms;

or a pharmaceutically acceptable ester of such compound;

or a pharmaceutically acceptable salt thereof.

The substituted methyl aryl or heteroaryl amide compounds of this invention have an antagonistic action towards prostaglandin and are thus useful in therapeutics, particularly for the treatment of a disorder or condition selected from the group consisting of pain, neuropathic pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures, bone fracture, immune and autoimmune diseases; cellular neoplastic transformations or metastic tumor growth; diabetic retinopathy, tumor angiogenesis; prostanoid-induced smooth muscle contraction associated with dysmenorrhea, premature labor, allergic rhinitis, atopic dermatitis, asthma or eosinophil related disorders, hyperimmunoglobulinaemia, Castleman's disease, myeloma; Alzheimer's disease, sleep disorders, endocrine disturbance; glaucoma; promotion of bone formation; cytoprotection in peptic ulcers, gastritis, regional enteritis, ulcerative colitis, diverticulitis or other gastrointestinal lesions; GI bleeding and patients undergoing chemotherapy; coagulation disorders selected from hypoprothrombinemia, haemophilia, other bleeding problems; thrombosis; occlusive vascular disease; presurgery; and anti-coagulation; sympathetically maintained pain; pain resulting from amputation, skin conditions (e.g. eczema, psoriasis); ophthalmic diseases such as glaucoma, retinitis, retinopathies, uveitis and of acute injury to the eye tissue (e.g. conjunctivitis); lung disorders (e.g. bronchitis, emphysema, allergic rhinitis, respiratory distress syndrome pigeon fancier's disease, farmer's lung, COPD); gastrointestinal tract disorders (e.g. aphthous ulcer, Crohn's disease atopic gastritis, gastritis varialoforme, ulcerative colitis, coeliac disease, regional ileitis, irritable bowel syndrome, inflammatory bowel disease, gastrointestinal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, tendonitis, bursitis, and Sjogren's; abnormal platelet function (e.g. occlusive vascular diseases); diuretic action; impotence or erectile dysfunction; bone disease characterised by abnormal bone metabolism or resorption such as osteoporosis, hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis; the hemodynamic side effects of NSAIDs and COX-2 inhibitors, cardiovascular diseases, hypertention or myocardiac ischemia; functional or organic venous insufficiency; varicose therapy; haemorrhoids; and shock states associated with a marked drop in arterial pressure (e.g. septic shock); neurodegenerative diseases and neurodegeneration such as dementia, particularly degenerative dementia (including senile dementia, Alzheimer's disease, Pick's disease, Huntingdon's chorea, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mile cognitive impairment associated with ageing, particularly Age Associated Memory Impairment; neuroprotection, neurodegeneration following stroke, cardiac arrest, pulmonary bypass, traumatic brain injury, spinal cord injury; tinnitus, complications of Type 1 diabetes (e.g. diabetic microangiopathy, diabetic nephropathy, macular degeneration, glaucoma), nephrotic syndrome, aplastic anaemia, uveitis, Kawasaki disease and sarcoidosi; kidney dysfuncion (e.g. nephritis particularly mesangial proliferative glomerulonephritis, nephritic syndrome), liver dysfunction (hepatitis, cirrhosis), gastrointestinal dysfunction (diarrhea), alcoholic cirrhosis, amyloidosis, atherosclerosis, cardiac disease, sclerosis, organ transplantation reactions, glucocorticoid induced osteoporosis, tooth loss, bone fractures, multiple myeloma, various edema, hypertension, premenstrual tension, urinary calculus, oliguria, hyperphosphaturia, prutitus urticaria, contact-type dermatitis, rhus dermatitis, pollakiuria, learning disability, gingiritis, predontitis, lung injury, liver injury, and constipation, or the like in mammalian, especially humans.

The compounds of formula (I) are also useful in preventing or reducing dependence on, or preventing or reducing tolerance or reverse tolerance to, a dependence-inducing agent. Examples of dependence inducing agents include opioids (e.g. morphine), CNS depressants (e.g. ethanol), psychostimulants (e.g. cocaine) and nicotine.

The compounds of formula (I) have also diuretic activity with a various characteristic such as a lower kaluretic activity relative to natriuretic effect, a larger phosphorus excretion.

Preferably, the substituted methyl aryl or heteroaryl amide compounds of this invention have an antagonistic action towards prostaglandin and are thus useful in therapeutics, particularly for the treatment of a disorder or condition selected from the group consisting of pain or inflammation associated with rheumatic fever, influenza or other viral infections, common cold, low back and neck pain, skeletal pain, dysmenorrhea, headache, migraine, toothache, sprains and strains, myositis, neuralgia, fibromyalgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures, bone fracture, immune and autoimmune diseases; cellular neoplastic transformations or metastic tumor growth; diabetic retinopathy, tumor angiogenesis; prostanoid-induced smooth muscle contraction associated with dysmenorrhea, premature labor, allergic rhinitis, atopic dermatitis, asthma or eosinophil related disorders; skin conditions (e.g. eczema, psoriasis); lung disorders (e.g. bronchitis, emphysema, allergic rhinitis, respiratory distress syndrome pigeon fancier's disease, farmer's lung, COPD); gastrointestinal tract disorders (e.g. aphthous ulcer, Crohn's disease atopic gastritis, gastritis varialoforme, ulcerative colitis, coeliac disease, regional ileitis, irritable bowel syndrome, inflammatory bowel disease, gastrointestinal reflux disease); diuretic action; bone disease characterised by abnormal bone metabolism or resorption such as osteoporosis, hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia and cancer cacchexia.

The compounds of the present invention are useful for the general treatment of pain, particularly inflammatory or neuropathic pain. Physiological pain is an important protective mechanism designed to warn of danger from potentially injurious stimuli from the external environment. The system operates through a specific set of primary sensory neurones and is exclusively activated by noxious stimuli via peripheral transducing mechanisms (Millan 1999 Prog. Neurobio. 57: 1-164 for an integrative Review). These sensory fibres are known as nociceptors and are characterised by small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptive input is transferred after complex processing in the dorsal horn, either directly or via brain stem relay nuclei to the ventrobasal thalamus and then on to the cortex, where the sensation of pain is generated.

Intense acute pain and chronic pain may involve the same pathways driven by pathophysiological processes and as such cease to provide a protective mechanism and instead contribute to debilitating symptoms associated with a wide range of disease states. Pain is a feature of many trauma and disease states. When a substantial injury, via disease or trauma, to body tissue occurs the characteristics of nociceptor activation are altered. There is sensitisation in the periphery, locally around the injury and centrally where the nociceptors terminate. This leads to hypersensitivity at the site of damage and in nearby normal tissue. In acute pain these mechanisms can be useful and allow for the repair processes to take place and the hypersensitivity returns to normal once the injury has healed. However, in many chronic pain states, the hypersensitivity far outlasts the healing process and is normally due to nervous system injury. This injury often leads to maladaptation of the afferent fibres (Woolf & Salter 2000 Science 288: 1765-1768). Clinical pain is present when discomfort and abnormal sensitivity feature among the patient's symptoms. Patients tend to be quite heterogeneous and may present with various pain symptoms. There are a number of typical pain subtypes: 1) spontaneous pain which may be dull, burning, or stabbing; 2) pain responses to noxious stimuli are exaggerated (hyperalgesia); 3) pain is produced by normally innocuous stimuli (allodynia) (Meyer et al., 1994 Textbook of Pain 13-44). Although patients with back pain, arthritis pain, CNS trauma, or neuropathic pain may have similar symptoms, the underlying mechanisms are different and, therefore, may require different treatment strategies. Therefore pain can be divided into a number of different areas because of differing pathophysiology, these include nociceptive, inflammatory, neuropathic pain etc. It should be noted that some types of pain have multiple aetiologies and thus can be classified in more than one area, e.g. Back pain, Cancer pain have both nociceptive and neuropathic components.

Nociceptive pain is induced by tissue injury or by intense stimuli with the potential to cause injury. Pain afferents are activated by transduction of stimuli by nociceptors at the site of injury and sensitise the spinal cord at the level of their termination. This is then relayed up the spinal tracts to the brain where pain is perceived (Meyer et al., 1994 Textbook of Pain 13-44). The activation of nociceptors activates two types of afferent nerve fibres. Myelinated A-delta fibres transmitted rapidly and are responsible for the sharp and stabbing pain sensations, whilst unmyelinated C fibres transmit at a slower rate and convey the dull or aching pain. Moderate to severe acute nociceptive pain is a prominent feature of, but is not limited to pain from strains/sprains, post-operative pain (pain following any type of surgical procedure), posttraumatic pain, burns, myocardial infarction, acute pancreatitis, and renal colic. Also cancer related acute pain syndromes commonly due to therapeutic interactions such as chemotherapy toxicity, immunotherapy, hormonal therapy and radiotherapy. Moderate to severe acute nociceptive pain is a prominent feature of, but is not limited to, cancer pain which may be tumor related pain, (e.g. bone pain, headache and facial pain, viscera pain) or associated with cancer therapy (e.g. postchemotherapy syndromes, chronic postsurgical pain syndromes, post radiation syndromes), back pain which may be due to herniated or ruptured intervertabral discs or abnormalities of the lumber facet joints, sacroiliac joints, paraspinal muscles or the posterior longitudinal ligament.

Neuropathic pain is defined as pain initiated or caused by a primary lesion or dysfunction in the nervous system (IASP definition). Nerve damage can be caused by trauma and disease and thus the term 'neuropathic pain' encompasses many disorders with diverse aetiologies. These include but are not limited to, Diabetic neuropathy, Post herpetic neuralgia, Back pain, Cancer neuropathy, HIV neuropathy, Phantom limb pain, Carpal Tunnel Syndrome, chronic alcoholism, hypothyroidism, trigeminal neuralgia, uremia, or vitamin deficiencies. Neuropathic pain is pathological as it has no protective role. It is often present well after the original cause has dissipated, commonly lasting for years, significantly decreasing a patients quality of life (Woolf and Mannion 1999 Lancet 353: 1959-1964). The symptoms of neuropathic pain are difficult to treat, as they are often heterogeneous even between patients with the same disease (Woolf & Decosterd 1999 Pain Supp. 6: S141-S147; Woolf and Mannion 1999 Lancet 353: 1959-1964). They include spontaneous pain, which can be continuous, or paroxysmal and abnormal evoked pain, such as hyperalgesia (increased sensitivity to a noxious stimulus) and allodynia (sensitivity to a normally innocuous stimulus).

The inflammatory process is a complex series of biochemical and cellular events activated in response to tissue injury or the presence of foreign substances, which result in swelling and pain (Levine and Taiwo 1994: Textbook of Pain 45-56). Arthritic pain makes up the majority of the inflammatory pain population. Rheumatoid disease is one of the commonest chronic inflammatory conditions in developed countries and rheumatoid arthritis is a common cause of disability. The exact aetiology of RA is unknown, but current hypotheses suggest that both genetic and microbiological factors may be important (Grennan & Jayson 1994 Textbook of Pain 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder 2002 Ann Pharmacother. 36: 679-686; McCarthy et al., 1994 Textbook of Pain 387-395). Most patients with OA seek medical attention because of pain. Arthritis has a significant impact on psychosocial and physical function and is known to be the leading cause of disability in later life. Other types of inflammatory pain include but are not limited to inflammatory bowel diseases (IBD), Other types of pain include but are not limited to;

Musculo-skeletal disorders including but not limited to myalgia, fibromyalgia, spondylitis, sero-negative (non-rheumatoid) arthropathies, non-articular rheumatism, dystrophinopathy, Glycogenolysis, polymyositis, pyomyositis.

Central pain or 'thalamic pain' as defined by pain caused by lesion or dysfunction of the nervous system including but not limited to central post-stroke pain, multiple sclerosis, spinal cord injury, Parkinson's disease and epilepsy.

Heart and vascular pain including but not limited to angina, myocardical infarction, mitral stenosis, pericarditis, Raynaud's phenomenon, scleredoma, scleredoma, skeletal muscle ischemia.

Visceral pain, and gastrointestinal disorders. The viscera encompasses the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders include the functional bowel disorders (FBD) and the inflammatory bowel diseases (IBD). These GI disorders include a wide range of disease states that are currently only moderately controlled, including—for FBD, gastro-esophageal reflux, dyspepsia, the irritable bowel syndrome (IBS) and functional abdominal pain syndrome (FAPS), and—for IBD, Crohn's disease, ileitis, and ulcerative colitis, which all regularly produce visceral pain. Other types of visceral pain include the pain associated with dysmenorrhea, pelvic pain, cystitis and pancreatitis.

Head pain including but not limited to migraine, migraine with aura, migraine without aura cluster headache, tension-type headache.

Orofacial pain including but not limited to dental pain, temporomandibular myofascial pain.

The present invention provides a pharmaceutical composition for the treatment of disease conditions mediated by prostaglandin, in a mammalian subject, which comprises administering to said subject a therapeutically effective amount of a compound of formula (I).

Further, the present invention also provides a composition which comprises a therapeutically effective amount of the substituted methyl aryl or heteroaryl amide compound of formula (I) or its pharmaceutically acceptable salt together with a pharmaceutically acceptable carrier. Among them, the composition is preferably for the treatment of disease defined above.

Also, the present invention provides for the use of a compound of formula (I), or a pharmaceutically acceptable ester of such compound, or a pharmaceutically acceptable salt thereof, as a medicament.

Also, the present invention provides a method for the treatment of disease conditions defined above, which comprises administering to said subject a therapeutically effective amount of a compound of formula (I).

Further, the present invention provides a method for the treatment of disease conditions defined above in a mammal, preferably human, which comprises administering to said subject a therapeutically effective amount of a compound of formula (I).

Yet further, the present invention provides the use of a therapeutically effective amount of a compound of formula (I) in the manufacture of a medicament for the treatment of the disease conditions defined above.

DETAILED DESCRIPTION OF THE INVENTION

As used herein, the term "halogen" means fluoro, chloro, bromo and iodo, preferably fluoro or chloro.

As used herein, the term "alkyl" means straight or branched chain saturated radicals, including, but not limited to methyl, ethyl, n-propyl, isopropyl, n-butyl, iso-butyl, secondary-butyl, tertiary-butyl.

As used herein, the term "alkylene", as used herein, means a saturated hydrocarbon (straight chain or branched) wherein a hydrogen atom is removed from each of the terminal carbons such as methylene, ethylene, methylethylene, propylene, butylene, pentylene, hexylene and the like.

As used herein, the term "alkenyl" means a hydrocarbon radical having at least one double bond including, but not limited to, ethenyl, propenyl, 1-butenyl, 2-butenyl and the like.

As used herein, the term "alkynyl", means a hydrocarbon radical having at least one triple bond including, but not limited to, ethynyl, propynyl, 1-butynyl, 2-butynyl and the like.

As used herein, the term "alkoxy" means alkyl-O—, including, but not limited to methoxy, ethoxy, n-propoxy, isopropoxy, n-butoxy, isobutoxy, secondary-butoxy, tertiary-butoxy.

As used herein, the term "cycloalkyl", means a saturated carbocyclic radical ring of 3 to 7 carbon atoms, including, but not limited to, cyclopropyl, cyclobutyl, cyclohexyl, cycloheptyl and the like.

As used herein, the term "alkanoyl" means a group having carbonyl such as R'—C(O)— wherein R' is $C_{1-4}$ alkyl or $C_{3-4}$ cycloalkyl, including, but not limited to formyl, acetyl, ethyl-C(O)—, n-propyl-C(O)—, isopropyl-C(O)—, n-butyl-C(O)—, iso-butyl-C(O)—, secondary-butyl-C(O)—, tertiary-butyl-C(O)—, cyclopropyl-C(O)—, cyclobutyl-C(O)— and the like.

As used herein, the term "haloalkyl", means an alkyl radical which is substituted by halogen atoms as defined above including, but not limited to, fluoromethyl, difluoromethyl, trifluoromethyl, 2-fluoroethyl, 2,2-difluoroethyl, 2,2,2-trifluoroethyl, 2,2,2-trichloroethyl, 3-fluoropropyl, 4-fluorobutyl, chloromethyl, trichloromethyl, iodomethyl and bromomethyl groups and the like.

As used herein, the term "haloalkoxy", as used herein, means haloalkyl-O—, including, but not limited to, fluoromethoxy, difluoromethoxy, trifluoromethoxy, 2-fluoroethoxy, 2,2-difluoroethoxy, 2,2,2-trifluoroethoxy, 2,2,2-trichloroethoxy, 3-fluoropropoxy, 4-fluorobutoxy, chloromethoxy, trichloromethoxy, iodomethoxy and bromomethoxy groups and the like.

As used herein the term "heterocyclic" means a 4 to 7-membered aromatic, partially saturated, or fully saturated hetero mono-cyclic ring, which contains either from 1 to 4 ring nitrogen heteroatoms or from 0 to 2 nitrogen ring heteroatoms and 1 oxygen or 1 sulfur ring heteroatom. Examples of such heterocycles include, but are not limited to, pyrazolyl, furyl, thienyl, oxazolyl, tetrazolyl, thiazolyl, imidazolyl, thiadiazolyl, pyridyl, pyrimidinyl, pyrrolyl, thiophenyl, pyrazinyl, pyridazinyl, isooxazolyl, isothiazolyl, triazolyl, furazanyl, piperidyl, piperidino, pyrrolidinyl, pyrrolidino, trahydrofuranyl, piperazinyl, morpholinyl, morpholino or tetrahydropyranyl.

Where the compounds of formula (I) contain hydroxy groups, they may form esters. Examples of such esters include esters with a hydroxy group and esters with a carboxy group. The ester residue may be an ordinary protecting group or a protecting group which can be cleaved in vivo by a biological method such as hydrolysis.

The term "esters" means a protecting group which can be cleaved in vivo by a biological method such as hydrolysis and forms a free acid or salt thereof. Whether a compound is such a derivative or not can be determined by administering it by intravenous injection to an experimental animal, such as a rat or mouse, and then studying the body fluids of the animal to determine whether or not the compound or a pharmaceutically acceptable salt thereof can be detected. Preferred examples of groups for an ester of a carboxyl group or a hydroxy group include: (1) aliphatic alkanoyl groups, for example: alkanoyl groups such as the formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoy, heptadecanoyl, 15-methylhexadecanoyl, octadecanoyl, 1-methylheptadecanoyl, nonadecanoyl, icosanoyl and henicosanoyl groups; halogenated alkylcarbonyl groups such as the chloroacetyl, dichloroacetyl, trichloroacetyl, and trifluoroacetyl groups; alkoxyalkanoyl groups such as the methoxyacetyl group; and unsaturated alkanoyl groups such as the acryloyl, propioloyl, methacryloyl, crotonoyl, isocrotonoyl and (E)-2-methyl-2-butenoyl groups; (2) aromatic alkanoyl groups, for example: arylcarbonyl groups such as the benzoyl, α-naphthoyl and β-naphthoyl groups; halogenated arylcarbonyl groups such as the 2-bromobenzoyl and 4-chlorobenzoyol groups; alkylated arylcarbonyl groups such as the 2,4,6-trimethylbenzoyl and 4-toluoyl groups; alkoxylated arylcarbonyl groups such as the 4-anisoyl group; nitrated arylcarbonyl groups such as the 4-nitrobenzoyl and 2-nitrobenzoyl groups; alkoxycarbonylated arylcarbonyl groups such as the 2-(methoxycarbonyl)benzoyl group; and arylated arylcarbonyl groups such as the 4-phenylbenzoyl group; (3) alkoxycarbonyl groups, for example: alkoxycarbonyl groups such as the methoxycarbonyl, ethoxycarbonyl, propoxycarbonyl, butoxycarbonyl, sec-butoxycarbonyl, t-butoxycarbonyl and isobutoxycarbonyl groups; and halogen- or tri(alkyl)silyl-substituted alkoxycarbonyl groups such as the 2,2,2-trichloroethoxycarbonyl and 2-trimethylsilylethoxycarbonyl groups; tetrahydropyranyl or tetrahydrothiopyranyl groups such as: tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl groups; tetrahydrofuranyl or tetrahydrothiofuranyl groups such as: tetrahydrofuran-2-yl and tetrahydrothiofuran-2-yl groups; (5) silyl groups, for example: tri(alkyl)silyl groups such as the trimethylsilyl, triethylsilyl, isopropyldimethylsilyl, t-butyldimethylsilyl, methyldiisopropylsilyl, methyldi-t-butylsilyl and triisopropylsilyl groups; and silyl groups substituted by one or more aryl and alkyl groups such as the diphenylmethylsilyl, diphenylbutylsilyl, diphenylisopropylsilyl and phenyldiisopropylsilyl groups; (6) alkoxymethyl groups, for example: alkoxymethyl groups such as the methoxymethyl, 1,1-dimethyl-1-methoxymethyl, ethoxymethyl, propoxymethyl, isopropoxymethyl, butoxymethyl and t-butoxymethyl groups; alkoxylated alkoxymethyl groups such as the 2-methoxyethoxymethyl group; and halo(alkoxy)methyl groups such as the 2,2,2-trichloroethoxymethyl and bis(2-chloroethoxy)methyl groups; (7) substituted ethyl groups, for example: alkoxylated ethyl groups such as the 1-ethoxyethyl and 1-(isopropoxy)ethyl groups; and halogenated ethyl groups such as the 2,2,2-trichloroethyl group; (8) aralkyl groups, for example: alkyl groups substituted by from 1 to 3 aryl groups such as the benzyl, α-naphthylmethyl, β-naphthylmethyl, diphenylmethyl, triphenylmethyl, α-naphthyldiphenylmethyl and 9-anthrylmethyl groups; alkyl groups substituted by from 1 to 3 substituted aryl groups, where one or more of the aryl groups is substituted by one or more alkyl, alkoxy, nitro, halogen or cyano substituents such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl and 4-cyanobenzyl groups; alkenyloxycarbonyl groups such as the vinyloxycarbonyl; aryloxycarbonyl groups such as phenoxycaronyl; and aralkyloxycarbonyl groups in which the aryl ring may be substituted by 1 or 2 alkoxy or nitro groups, such as benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

A preferred compound of formula (I) of this invention is that wherein Y represents $NR^4$ or an oxygen atom; and $R^4$ represents an alkyl group having from 1 to 3 carbon atoms. More preferably, Y represents $NCH_3$ or an oxygen atom. Most preferably, Y represents an oxygen atom A preferred compound of formula (I) of this invention is that wherein Z represents a halogen atom. More preferably, Z represents a chlorine atom or a fluorine atom.

A preferred compound of formula (I) of this invention is that wherein $R^1$ represents an alkyl group having from 1 to 6 carbon atoms; a cycloalkyl group having from 3 to 7 carbon atoms, a phenyl group optionally substituted with one or more substituents α; or a group $Het^1$ optionally substituted with one or more substituents α; $Het^1$ represents a heterocyclic group having from 5 to 6 ring atoms which contains either from 1 to 2 ring nitrogen heteroatoms or from 0 to 2 nitrogen ring heteroatoms and 1 oxygen or 1 sulfur ring heteroatom; said substituents α are selected from the group consisting of halogen atoms, alkyl groups having from 1 to 4 carbon atoms, haloalkyl groups having from 1 to 4 carbon atoms, hydroxy groups, alkoxy groups having from 1 to 4 carbon atoms, haloalkoxy groups having from 1 to 4 carbon atoms, cyano groups, hydroxy alkyl groups having from 1 to 4 carbon atoms, alkoxyalkyl groups having from 1 to 4 carbon atoms in alkoxy and alky groups, alkylsulfonyl groups having from 1 to 4 carbon atoms and alkanoyl groups having from 2 to 5 carbon atoms. More preferably, $R^1$ represents an alkyl group having from 1 to 6 carbon atoms, a cycloalkyl group having from 4 to 6 carbon atoms, a phenyl group, a pyridyl group, an oxazolyl group, a pyrazolyl group, a thiazolyl group, a tetrahydrofuranyl group or a tetrahydropyranyl group; said phenyl group, pyridyl group, oxazolyl group, pyrazolyl group, thiazolyl group, tetrahydrofuranyl group and tetrahydropyranyl group referred to in the definitions of $R^1$ are unsubstituted or are substituted by at least one substituent selected from the group consisting of substituents α; said substituents α are selected from the group consisting of halogen atoms, alkyl groups having from 1 to 2 carbon atoms and cyano groups. More preferably, $R^1$ represents a butyl group, a pyridyl group, a phenyl group, an oxazolyl group, a pyrazolyl group or a thiazolyl group; said phenyl group, pyridyl group, oxazolyl group, pyrazolyl group, thiazolyl group referred to in the definitions of $R^1$ are unsubstituted or are substituted by 1 to 2 substituent selected from the group consisting of substituents α; said substituents α are selected from the group consisting of halogen atoms and alkyl groups having from 1 to 2 carbon atoms. Most preferably, $R^1$ represents a phenyl group, optionally substituted by 1 to 2 groups independently selected from a fluorine atom, a chlorine atom and a methyl group.

A preferred compound of formula (I) of this invention is that wherein $R^2$ and $R^3$ independently represent a hydrogen atom or an alkyl group having from 1 to 3 carbon atoms. More preferably, $R^2$ represents a hydrogen atom; and $R^3$ represents a methyl group.

Particularly preferred compounds of the invention include those in which each variable in Formula (I) is selected from the preferred groups for each variable. Even more preferable compounds of the invention include those where each variable in Formula (I) is selected from the more preferred groups for each variable.

A preferred individual compound of this invention is selected from

4-[(1S)-1-({5-Chloro-2-[(4-chlorophenoxy)methyl]benzoyl}amino)ethyl]benzoic acid;
4-[(1S)-1-({5-Chloro-2-[(4-methylphenoxy)methyl]benzoyl}amino)ethyl]benzoic acid;
4-[(1S)-1-({5-Chloro-2-[(3-chlorophenoxy)methyl]benzoyl}amino)ethyl]benzoic acid;
4-[(1S)-1-({5-Chloro-2-[(4-fluorophenoxy)methyl]benzoyl}amino)ethyl]benzoic acid;
4-[(1S)-1-({5-Chloro-2-[(2,3-difluorophenoxy)methyl]benzoyl}amino)ethyl]benzoic acid;
4-[(1S)-1-({5-Chloro-2-[(3,4-difluorophenoxy)methyl]benzoyl}amino)ethyl]benzoic acid;
4-[(1S)-1-({5-Chloro-2-[(2,4-difluorophenoxy)methyl]benzoyl}amino)ethyl]benzoic acid;
4-{(1S)-1-[({5-Chloro-2-[(3-chlorophenoxy)methyl]pyridin-3-yl}carbonyl)amino]ethyl}benzoic acid;
4-[(1S)-1-({5-Chloro-2-[(2-chlorophenoxy)methyl]benzoyl}amino)ethyl]benzoic acid;
4-[(1S)-1-({5-Chloro-2-[(3,5-difluorophenoxy)methyl]benzoyl}amino)ethyl]benzoic acid;
4-{(1S)-1-[({5-Chloro-2-[(4-chlorophenoxy)methyl]pyridin-3-yl}carbonyl)amino]ethyl}benzoic acid;
4-[(1S)-1-({5-Chloro-2-[(3-fluorophenoxy)methyl]benzoyl}amino)ethyl]benzoic acid;
4-[(1S)-1-({5-Chloro-2-[(2,6-difluorophenoxy)methyl]benzoyl}amino)ethyl]benzoic acid;
4-[(1S)-1-({5-Chloro-2-[(2-fluorophenoxy)methyl]benzoyl}amino)ethyl]benzoic acid;
4-[(1S)-1-({5-Chloro-2-[(2,5-difluorophenoxy)methyl]benzoyl}amino)ethyl]benzoic acid; and
4-{(1S)-1-[({2-[(4-Chlorophenoxy)methyl]-5-fluoropyridin-3-yl}carbonyl)amino]ethyl}benzoic acid;

or a pharmaceutically acceptable ester of such compound; or a pharmaceutically acceptable salt thereof.

General Synthesis

The compounds of formula I of the present invention may be prepared according to known preparation methods, or General Procedures or preparation methods illustrated in the following reaction schemes. Unless otherwise indicated $R^1$ through $R^3$ and X, Y, and Z in the reaction schemes and discussion that follow are defined as above. The term "protecting group", as used hereinafter, means a hydroxy or amino protecting group which is selected from typical hydroxy or amino protecting groups described in Protective Groups in Organic Synthesis edited by T. W. Greene et al. (John Wiley & Sons, 1999);

The following reaction schemes illustrate the preparation of compounds of formula (I).

Scheme 1:

This illustrates the preparation of compounds of formula (I).

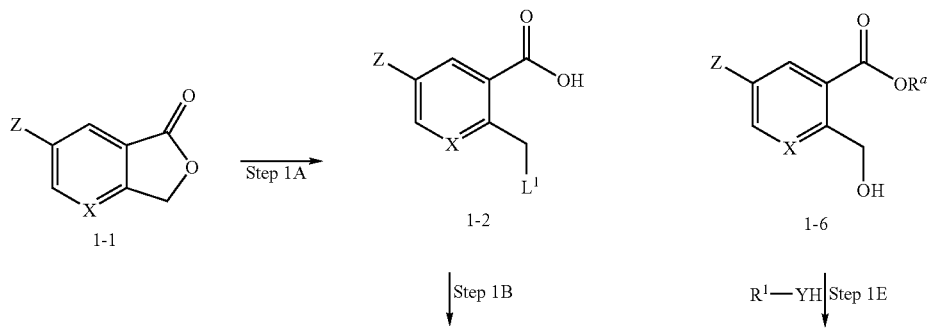

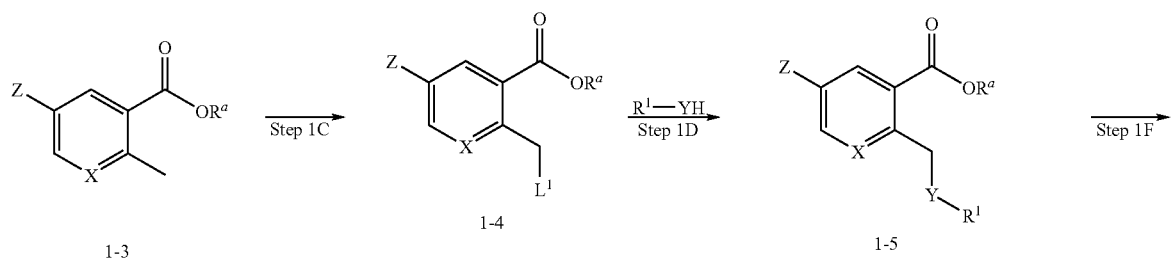

-continued

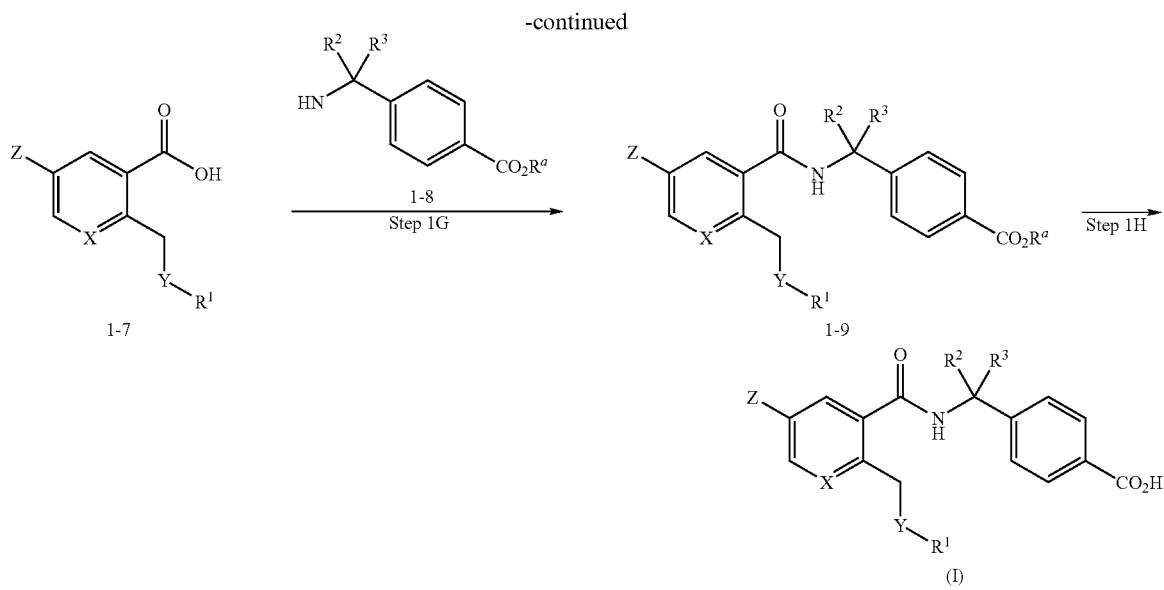

In the above formula, $R^a$ represents an alkyl group having from 1 to 4 carbon atoms. $L^1$ represents a leaving group. Examples of suitable leaving groups include: halogen atoms, such as chlorine, bromine and iodine; sulfonic esters such as TfO (triflates), MsO (mesylates), TsO (tosylates); and the like.

Step 1A

In this step, a compound of the formula 1-2 in which $L^1$ represents a halogen atom can be prepared by the halogenating the compound of the formula 1-1 under halogenation conditions with a halogenating reagent in a reaction-inert solvent.

Examples of suitable solvents include: acetic acid, water, acetonitrile, and dichloromethane. Preferred halogenating agents include: chlorinating agents; such as hydrogen chloride, chlorine, and acetyl chloride, brominating agents, such as hydrogen bromide, bromine, and boron tribromide, iodinating agents; hydrogen iodide, trimethylsilyl iodide, sodium iodide-boron tribromide. The reaction can be carried out at a temperature of from 0° C. to 200° C., more preferably from 20° C. to 120° C. Reaction times are, in general, from 5 minutes to 24 hours, more preferably 30 minutes to 10 hours, will usually suffice.

Step 1B

In this Step, an ester compound of formula 1-4 can be prepared by the esterification of the acid compound of formula 1-2.

The esterification may be carried out by a number of standard procedures known to those skilled in the art (e.g., *Protective Groups in Organic Synthesis*, Third edition. ed. T. W. Green and P. G. M. Wuts, Wiley-Interscience., pp 373-377.). Typical esterification can be carried out in the presence of an acid catalyst, e.g. sulfuric acid, p-toluenesulfonic acid, camphorsulfonic acid and benzenesulfonic acid, in a suitable reaction-inert solvent, e.g. methanol or ethanol. Typical esterification can also be carried out with a suitable $C_{1-6}$ alkylhalide or benzylhalide in the presence of a base, $K_2CO_3$, $Cs_2CO_3$, $NaHCO_3$ and DBU, in a suitable reaction-inert solvent, e.g. ethers such as tetrahydrofuran, 1,2-dimethoxyethane, diethyl ether, diisopropyl ether, diphenyl ether, DMF, DMSO, R'OH and 1,4-dioxane. The esterification also carried out with trimethylsilyidiazomethane in a suitable reaction-inert solvent, e.g. methanol, benzene and toluene. The esterification also carried out with diazomethane in a suitable reaction-inert solvent, e.g. diethyl ether. Alternatively, the esterification may be carried out with R'OH, in the presence of a coupling agent, e.g. DCC, WSC, diisoproopylcyanophosphonate (DIPC), BOPCI and 2,4,6-trichlorobenzoic acid chloride, and a tertiaryamine, e.g. i-$Pr_2$Net or $Et_3N$, in a suitable solvent, e.g. DMF, THF, diethyl ether, DME, dichloromethane and DCE.

Step 1C

Alternatively, in this step, the compound of the formula 1-4 in which $L^1$ represents a halogen atom can also be prepared by the halogenating the compound of a formula 1-3 under halogenation conditions with a halogenating reagent in a reaction-inert solvent.

Examples of suitable solvents include: tetrahydrofuran, 1,4-dioxane, N,N-dimethylformamide, acetonitrile; alcohols, such as methanol or ethanol; halogenated hydrocarbons, such as dichloromethane, 1,2-dichloroethane, chloroform or carbon tetrachloride and acetic acid. Suitable halogenating reagents include, for example, bromine, chlorine, iodine, N-chlorosuccimide, N-bromosuccimide, 1,3-dibromo-5,5-dimethylhydantoin, bis(dimethylacetamide)hydrogen tribromide, tetrabutylammonium tribromide, bromodimethylsulfonium bromide, hydrogen bromide-hydrogen peroxide, nitrodibromoacetonitrile or copper(II) bromide. The reaction can be carried out at a temperature of from 0° C. to 200° C., more preferably from 20° C. to 120° C. Reaction times are, in general, from 5 minutes to 48 hours, more preferably 30 minutes to 24 hours, will usually suffice.

Step 1D

In this step, a compound of formula 1-5 can be prepared by the alkylation of the compound of formula 1-4 with a compound of formula $R^1$—YH in the presence of a base in a reaction-inert solvent. Examples of suitable solvents include: tetrahydrofuran, N,N-dimethylformamide, dimethylsulfoxide, diethylether, toluene, ethylene glycol dimethylether generally or 1,4-dioxane. Examples of suitable bases include:

alkyl lithiums, such as n-butyllithium, sec-butyllithium or tert-butyllithium; aryllithiums, such as phenyllithium or lithium naphtilide; methalamide such as sodium amide or lithium diisopropylamide; and alkali metal, such as potassium hydride or sodium hydride. This reaction may be carried out at a temperature in the range from −50° C. to 200° C., usually from 0° C. to 80° C. for 5 minutes to 72 hours, usually 30 minutes to 24 hours.

Step 1E

Alternatively, in this step, the compound of formula 1-5 can also be prepared by Mitsunobu reaction of a compound of formula 1-6 with a compound of formula $R^1$—YH in the presence of dialkyl azodicarboxylate in a reaction-inert solvent. The compound of formula 1-6 may be treated with a compound of formula $R^1$—YH in the presence of dialkyl azodicarboxylate such as diethyl azodicarboxylate (DEAD) and phosphine reagent such as triphenylphosphine. Preferably, this reaction may be carried out in a reaction-inert solvent. Preferred reaction inert solvents include, but are not limited to, tetrahydrofuran (THF), diethyl ether, dimethylformamide (DMF), benzene, toluene, xylene, o-dichlorobenzene, nitrobenzene, dichloromethane, 1,2-dichloroethane, dimethoxyethane (DME), or mixtures thereof. This reaction may be carried out at a temperature in the range from −50° C. to 200° C., usually from 0° C. to 80° C. for 5 minutes to 72 hours, usually 30 minutes to 24 hours.

Step 1F

In this step, an acid compound of formula 1-7 may be prepared by hydrolysis of the ester compound of formula 1-5 in a solvent.

The hydrolysis may be carried out by conventional procedures. In a typical procedure, the hydrolysis carried out under the basic condition, e.g. in the presence of sodium hydroxide, potassium hydroxide or lithium hydroxide. Suitable solvents include, for example, alcohols such as methanol, ethanol, propanol, butanol, 2-methoxyethanol, and ethylene glycol; ethers such as tetrahydrofuran (THF), 1,2-dimethoxyethane (DME), and 1,4-dioxane; amides such as N,N-dimethylformamide (DMF) and hexamethylphospholictriamide; and sulfoxides such as dimethyl sulfoxide (DMSO). This reaction may be carried out at a temperature in the range from −20° C. to 100° C., usually from 20° C. to 75° C. for 30 minutes to 48 hours, usually 60 minutes to 30 hours.

The hydrolysis may also be carried out under the acidic condition, e.g. in the presence of hydrogen halides, such as hydrogen chloride and hydrogen bromide; sulfonic acids, such as p-toluenesulfonic acid and benzenesulfonic acid; pyridium p-toluenesulfonate; and carboxylic acid, such as acetic acid and trifluoroacetic acid. Suitable solvents include, for example, alcohols such as methanol, ethanol, propanol, butanol, 2-methoxyethanol, and ethylene glycol; ethers such as tetrahydrofuran (THF), 1,2-dimethoxyethane (DME), and 1,4-dioxane; halogenated hydrocarbons, such as dichloromethane, 1,2-dichloroethane, amides such as N,N-dimethylformamide (DMF) and hexamethylphospholictriamide; and sulfoxides such as dimethyl sulfoxide (DMSO). This reaction may be carried out at a temperature in the range from −20° C. to 100° C., usually from 0° C. to 65° C. for 30 minutes to 24 hours, usually 60 minutes to 10 hours.

Step 1G

In this step, an amide compound of formula 1-9 may be prepared by the coupling reaction of an amine compound of formula 1-8 with the acid compound of formula 1-7 in the presence or absence of a coupling reagent in an inert solvent. If desired, this reaction may be carried out in the presence or absence of an additive such as 1-hydoroxybenzotriazole (HOBt) or 1-hydroxyazabenzotriazole. Examples of suitable solvents include: acetone, nitromethane, N,N-dimethylformamide (DMF), sulfolane, dimethyl sulfoxide (DMSO), 1-methyl-2-pirrolidinone (NMP), 2-butanone, acetonitrile; halogenated hydrocarbons, such as dichloromethane, 1,2-dichloroethane, chloroform; and ethers, such as tetrahydrofuran and 1,4-dioxane. This reaction may be carried out at a temperature in the range from −20° C. to 100° C., more preferably from about 0° C. to 60° C. for 5 minutes to 1 week, more preferably 30 minutes to 24 hours, will usually suffice. Suitable coupling reagents are those typically used in peptide synthesis including, for example, diimides (e.g., dicyclohexylcarbodiimide (DCC), water soluble carbodiimide (WSC)), O-benzotriazol-1-yl-N,N,N',N'-tetramethyluronium hexafluorophosphate (HBTU), 2-ethoxy-N-ethoxycarbonyl-1,2-dihydroquinoline, 2-bromo-1-ethylpyridinium tetrafluoroborate (BEP), 2-chloro-1,3-dimethylimidazolinium chloride, benzotriazol-1-yloxy-tris(dimethylamino)phosphonium hexafluorophosphate (BOP), diethyl azodicarboxylate-triphenylphosphine, diethylcyanophosphate, diethylphosphorylazide, 2-chloro-1-methylpyridinium iodide, N, N'-carnbonyldiimidazole, benzotriazole-1-yl diethyl phosphate, ethyl chloroformate or isobutyl chloroformate. If desired, the reaction may be carried out in the presence of a base such as, N,N-diisopropylethylamine, N-methylmorpholine, 4-(dimethylamino)pyridine and triethylamine. The amide compound of formula (I) may be formed via an acylhalide, which may be obtained by the reaction with halogenating agents such as oxalylchloride, phosphorus oxychloride and thionyl chloride. The resulting acylhalide may be converted to the corresponding amide compound by treating with the amine compound of formula 1-13 under the similar conditions as described in this step.

Step 1H

In this Step, the compound of formula (I) may be prepared by hydrolysis of the ester compound of formula 1-9. This reaction is essentially the same as and may be carried out in the same manner as and using the same reagents and reaction conditions as Step 1F in Scheme 1.

Scheme 2:

This illustrates the preparation of compounds of formula (Ia) wherein X represents a nitrogen atom; and Y represents an oxygen atom.

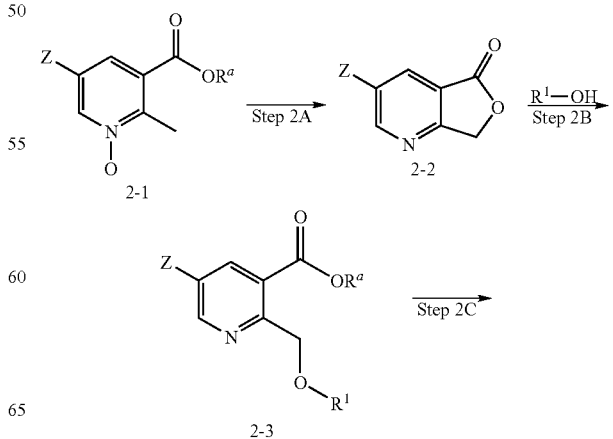

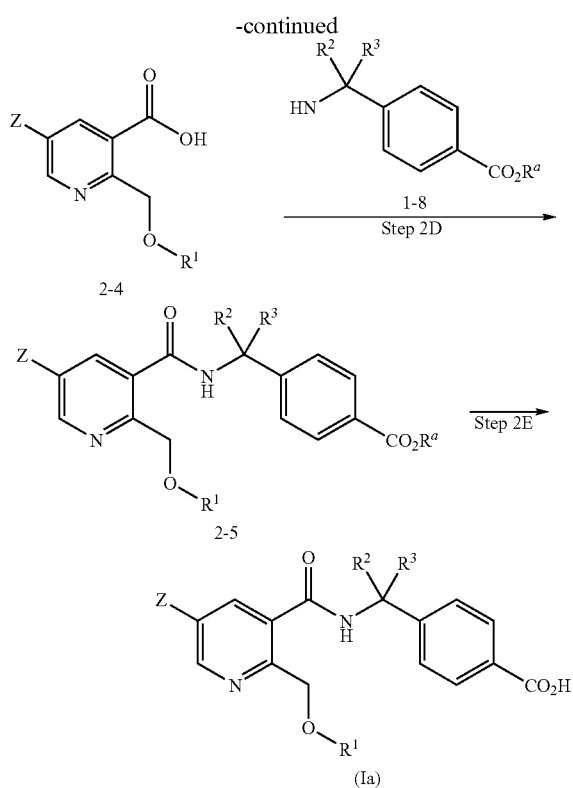

In the above formula, and $R^a$ is defined in Scheme 1.

Step 2A

In this Step, a lactone compound of formula 2-2 may be prepared by rearrangement of a compound of formula 2-1 followed by cyclization in a reaction-inert solvent.

Firstly, the compound 2-1 may be treated with an reagent in a reaction-inert solvent. Examples of suitable solvents include: such as dichloromethane and dimethylformamide. Examples of suitable reagents include: such as trifluoroacetic anhydride and acetic anhydride. The reaction can be carried out at a temperature of from −50° C. to 100° C., more preferably from −0° C. to 40° C. Reaction times are, in general, from 5 minutes to 48 hours, more preferably 30 minutes to 24 hours, will usually suffice.

Secondly, the obtained alcohol compound may be treated with a base or a acid in a reaction-inert solvent. Examples of suitable solvents include: such as methanol, benzene, toluene, and acetic acid. Example of such bases include: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine or dimethylaminopyridine. Example of such acids include: hydrogen halides, such as hydrogen chloride and hydrogen bromide; sulfonic acids, such as p-toluenesulfonic acid and benzenesulfonic acid; pyridium p-toluenesulfonate; and carboxylic acid, such as acetic acid and trifluoroacetic acid. The reaction can be carried out at a temperature of from 0° C. to 200° C., more preferably from room temperature to 100° C. Reaction times are, in general, from 5 minutes to 48 hours, more preferably 30 minutes to 24 hours, will usually suffice.

Step 2B

In this Step, a compound of formula 2-3 may be prepared by the reaction of the lactone compound of formula 2-2 with an alcohol compound of formula $R^1$—OH in the absence or the presence of a base in an inert solvent.

Examples of suitable solvents include: alcohols, such as methanol or ethanol; halogenated hydrocarbons, such as dichloromethane, 1,2-dichloroethane, chloroform or carbon tetrachloride and acetic acid; aromatic hydrocarbons, such as benzene, toluene, xylene, nitrobenzene, and pyridine; halogenated hydrocarbons, such as methylene chloride, chloroform, carbon tetrachloride and dichloroethane; ethers, such as diethyl ether, diisopropyl ether, DME, tetrahydrofuran and dioxane; ethyl acetate, acetonitrile, N,N-dimethylformamide, dimethylsulfoxide and water. Example of such bases include: an alkali or alkaline earth metal hydroxide, alkoxide, carbonate, halide or hydride, such as sodium hydroxide, potassium hydroxide, sodium methoxide, sodium ethoxide, potassium tert-butoxide, sodium carbonate, potassium carbonate, potassium fluoride, sodium hydride or potassium hydride, or an amine such as triethylamine, tributylamine, diisopropylethylamine, pyridine or dimethylaminopyridine in the presence or absence of a reaction-inert solvent.

The reaction can be carried out at a temperature of from −100° C. to 250° C., more preferably from D ° C. to the reflux temperature. Reaction times are, in general, from 1 minute to 10 day, more preferably from 20 minutes to 5 days, will usually suffice. from 1 minute to a day, preferably from 1 hour to 10 hours.

Step 2C

In this step, an acid compound of formula 2-4 may be prepared by hydrolysis of the compound of formula 2-3. This reaction is essentially the same as and may be carried out in the same manner as and using the same reagents and reaction conditions as Step 1F in Scheme 1.

Step 2D

In this Step, the compound of formula 2-5 may be prepared by the coupling reaction of the compound of formula 2-4 with the compound of formula 1-8 in an inert solvent.

This reaction is essentially the same as and may be carried out in the same manner as and using the same reagents and reaction conditions as Step 1G in Scheme 1.

Step 2E

In this Step, the compound of formula (Ia) may be prepared by hydrolysis of the ester compound of formula 2-5.

This reaction is essentially the same as and may be carried out in the same manner as and using the same reagents and reaction conditions as Step 1F in Scheme 1.

In the above Schemes from 1 and 2, examples of suitable solvents include a mixture of any two or more of those solvents described in each step.

The starting materials in the aforementioned general syntheses are commercially available or may be obtained by conventional methods known to those skilled in the art.

The compounds of formula (I), and the intermediates above-mentioned preparation methods can be isolated and purified by conventional procedures, such as recrystallization or chromatographic purification.

The various general methods described above may be useful for the introduction of the desired groups at any stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

(a) Method for Assessing Biological Activities:

In Vitro Assays

Human EP Receptor Cell Membrane Binding Assay:

Stable Expression of Human EP1, 2, 3 and 4 Receptors in the Human Embryonic Kidney (HEK293) Cell Line The cDNA clones of human EP1, 2, 3 and 4 receptors are obtained by polymerase chain reaction (PCR) from rat kidney or heart cDNA libraries (Clontech). Human embryonic kidney cells (HEK 293) are stably transfected with expression vectors for human EP1, 2, 3 and 4 receptors in according to the method described in the article; the journal of biological chemistry vol. 271 No. 39, pp 23642-23645.

Preparation of Membrane Fraction:

The EP1, 2, 3 and 4 transfectant are grown in Dulbecco's modified Eagle's medium containing 10% fetal bovine serum, 50 U/ml penicillin, 50 µg/ml streptomycin and 500 µg/ml G418 (selection medium) at 37° C. in a humidified atmosphere of 5% $CO_2$ in air. For the membrane preparation, cells are harvested with phosphate buffered saline (PBS) and centrifuged at 400×g for 5 min. The pellet is suspended with child (4° C.) PBS containing 1/100 volume of protease inhibitor cocktail (SIGMA) (1 mM (4-(2-aminoethyl)-benzenesulfonyl fluoride (AEBSF)), 0.8 µM Aprotinin, 22 µM Leupeptin, 40 µM Bestatin, 15 µM Pepstatin A and 14 µM E-64). Cells are lysed with ultrasonic cell disrupter for 60-sec sonication. Then cell mixtures are centrifuged at 1,000×g for 10 minutes. The supernatant is centrifuged at 160,000×g for 30 minutes at 4° C. The pellet is resuspended in assay buffer (10 mM 2-morpholinoethanesulfonic acid (MES)-KOH, 1 mM etylenediamine tetra-acetic acid (EDTA), 10 mM $MgCl_2$, pH 6.0), and protein concentration is determined by Bradford method (Bio-Rad assay). This membrane preparation is stored at −80° C. freezer until use for binding assay.

Binding Assay:

Membrane Binding Assay

[$^3$H]-$PGE_2$ membrane binding assays are performed in the reaction mixture of 10 mM MES/KOH (pH6.0), 10 mM $MgCl_2$, 1 mM EDTA, 1 nM [$^3$H]-$PGE_2$ (Amersham TRK431, 164 Ci/mmol), 2-10 µg of protein from membrane fraction (human EP1, 2, 3 and 4/HEK293 transfectant) and test compound (total volume is 0.1 ml in 96 well polypropylene plate). Incubation is conducted for 60 min at room temperature prior to separation of the bound and free radioligand by rapid filtration through glass fiber filters (Printed Filtermat B, 1205-404, glass fiber, double thickness, size 102×258 mm, Wallac inc., presoaked in 0.2% polyethylenimine). Filters are washed with assay buffer and the residual [$^3$H]-$PGE_2$ bound to the filter is determined by liquid scintillation counter (1205 Betaplate™). Specific binding is defined as the difference between total binding and nonspecific binding which is determined in the presence of 10 µM $PGE_2$.

cAMP Assay in Human $EP_4$ Transfectant

HEK293 cells expressing human $EP_4$ receptors ($hEP_4$ cells) are maintained in DMEM containing 10% FBS and 500 µg/ml geneticin. For harvesting $hEP_4$ cells, culture medium is aspirated and cells in 75 $cm^2$ flask are washed with 10 ml of phosphate buffered saline (PBS). Another 10 ml of PBS is added to the cells and incubated for 20 min at room temperature. Human $EP_4$ cells are harvested by pipetting and centrifuged at 300×g for 4 min. Cells are resuspended in DMEM without neutral red at a density of 7×10$^5$ cells/ml containing 0.2 mM IBMX (PDE inhibitor), 1 nM $PGE_2$ and test compounds in PCR-tubes, and incubated at 37° C. for 10 min. The reaction is stopped by heating at 100° C. for 10 min with thermal cycler. Concentration of cAMP in reaction mixtures is determined with SPA cAMP Kit (Amersham) or cAMP Screen™ (Applied Biosystems) according to the manufacture's instruction.

Reference: Eur. J. Pharmacol. 340 (1997) 227-241.

In Vivo Assays

Carrageenan Induced Mechanical Hyperalgesia in Rats:

Male 4-week-old SD rats were fasted over night. Hyperalgesia was induced by intraplantar injection of λ-carrageenin (0.1 ml of 1% w/v suspension in saline, Zushikagaku). The test compounds (1 ml of 0.1% methylcellulose/100 g body weight) were given per orally at 5.5 hours after the carrageenin injection. The mechanical pain threshold was measured by analgesy meter (Ugo Basile) at 4, 5, 6.5 and 7.5 hours after the carrageenin injection and the change of pain threshold was calculated.

Reference: Randall L. O. & Selitto I. J., Arch. Int. Pharmacodyn. 111, 409-419, 1957

Prostaglandin $E_2$($PGE_2$)-Induced Thermal Hyperalgesia in Rats:

Male 4-week-old SD rats were fasted over night. Hyperalgesia was induced by intraplantar injection of 100 ng of PGE2 in 0.05% ethanol/saline (100 ul) into the right hindpaw of the rats. Animals were given orally or intravenously either vehicle (po: 0.1% methyl cellulose, iv: 10% DMSO/saline) or a test compound prior to $PGE_2$ injection, respectively. Rats were placed in plastic cages of plantar test apparatus (Ugo Basile) and the mobile radiant heat source was focused on right hind paw of the rats. The thermal paw-withdrawal latency (sec.) was measured at 15 min after $PGE_2$ injection.

Reference: Hargreaves K. et al., Pain 32, 77-88, 1988.

CFA-Induced Weight Bearing Deficits in Rats:

Male 7-week-old SD rats were fasted over night. CFA (300 µg of *Mycobacterium Tuberculosis* H37 RA (Difco Laboratories) in 100 µL of liquid paraffin (Wako)) was injected into the rat's right hind footpad. Two days after the administration of CFA, the changes in hind paw weight distribution between the left (ipsilateral) and the right (contralateral) limbs were measured as an index of pain by using Linton Incapacitance tester (Linton Instrumentation, UK). The test compounds suspended in 0.1% MC (Wako) administered orally in a volume of 1 mL per 100 g body weight. Each animal was placed in the apparatus and the weight load exerted by the hind paws was measured before, 1, 2 and 4 hours after drug administration.

Formalin-Induced Licking/Biting Behavior in Rats:

Male 4-week-old SD rats were fasted over night. Animals were habituated to observation chambers for at least 15 min prior to testing. Licking/biting behavior was induced by intraplantar injection of formalin (0.05 ml of 2% w/v solution in saline, 37% Formaldehyde solution, Wako Chemicals). The test compounds (1 ml of 0.1% methylcellulose/100 g body weight) were given per orally at 1 hour before the formalin injection. Behavior of animals after formalin injection was recorded for 45 minutes using video camera. The time spent licking or biting the injection paw was counted by stopwatch and summed in 5 minutes bins for 45 minutes. The results are expressed as licking/biting time for the early phase (0-10 min) and the late phase (10-45 min).

Formalin-Induced Licking/Biting Behavior in Mice:

Male 4-week-old ddY mice were used. Animals were habituated to observation chambers for at least 30 min prior to testing. Licking/biting behavior was induced by intraplantar injection of formalin (0.02 ml of 2% w/v solution in saline, 37% Formaldehyde solution, Wako Chemicals). The test compounds (0.05 ml of 0.1% methylcellulose/10 g body weight) were given per orally at 1 hour before the formalin injection. Behavior of animals after formalin injection was recorded for 45 minutes using video camera. The time spent licking or biting the injection paw was counted by stopwatch and summed in 5 minutes bins for 45 minutes. The results are expressed as licking/biting time for the early phase (0-10 min) and the late phase (10-45 min).

Most of the compounds prepared in the working examples appearing hereafter demonstrate higher affinity for $EP_4$-receptors than for EP1, 2 and 3-receptors.

Caco-2 Permeability

Caco-2 permeability was measured according to the method described in Shiyin Yee, *Pharmaceutical Research*, 763 (1997).

Caco-2 cells were grown on filter supports (Falcon HTS multiwell insert system) for 14 days. Culture medium was removed from both the apical and basolateral compartments and the monolayers were preincubated with pre-warmed 0.3 ml apical buffer and 1.0 ml basolateral buffer for 0.75 hour at 37° C. in a shaker water bath at 50 cycles/min. The apical buffer consisted of Hanks Balanced Salt Solution, 25 mM D-glucose monohydrate, 20 mM MES Biological Buffer, 1.25 mM $CaCl_2$ and 0.5 mM $MgCl_2$ (pH 6.5). The basolateral buffer consisted of Hanks Balanced Salt Solution, 25 mM D-glucose monohydrate, 20 mM HEPES Biological Buffer, 1.25 mM $CaCl_2$ and 0.5 mM $MgCl_2$ (pH 7.4). At the end of the preincubation, the media was removed and test compound solution (10 µM) in buffer was added to the apical compartment. The inserts were moved to wells containing fresh basolateral buffer and incubated for 1 hr. Drug concentration in the buffer was measured by LC/MS analysis.

Flux rate (F, mass/time) was calculated from the slope of cumulative appearance of substrate on the receiver side and apparent permeability coefficient ($P_{app}$) was calculated from the following equation.

$$P_{app} (cm/sec) = (F*VD)/(SA*MD)$$

where SA is surface area for transport (0.3 $cm^2$), VD is the donor volume (0.3 ml), MD is the total amount of drug on the donor side at t=0. All data represent the mean of 2 inserts. Monolayer integrity was determined by Lucifer Yellow transport.

Human Dofetilide Binding

Cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells were homogenized using a Polytron homogenizer (at the maximum power for 20 seconds) and centrifuged at 48,000 g for 20 minutes at 4° C. The pellet was resuspended, homogenized and centrifuged once more in the same manner. The resultant supernatant was discarded and the final pellet was resuspended (10-fold volume of 50 mM Tris buffer) and homogenized at the maximum power for 20 seconds. The membrane homogenate was aliquoted and stored at −80° C. until use. An aliquot was used for protein concentration determination using a Protein Assay Rapid Kit and ARVO SX plate reader (Wallac). All the manipulation, stock solution and equipment were kept on ice at all time. For saturation assays, experiments were conducted in a total volume of 200 µl. Saturation was determined by incubating 20 µl of [$^3$H]-dofetilide and 160 µl of membrane homogenates (20-30 µg protein per well) for 60 min at room temperature in the absence or presence of 10 µM dofetilide at final concentrations (20 µl) for total or nonspecific binding, respectively. All incubations were terminated by rapid vacuum filtration over PEI soaked glass fiber filter papers using Skatron cell harvester followed by two washes with 50 mM Tris buffer (pH 7.5 at 25° C.). Receptor-bound radioactivity was quantified by liquid scintillation counting using Packard LS counter.

For the competition assay, compounds were diluted in 96 well polypropylene plates as 4-point dilutions in semi-log format. All dilutions were performed in DMSO first and then transferred into 50 mM Tris buffer (pH 7.5 at 25° C.) containing 1 mM $MgCl_2$, 10 mM KCl so that the final DMSO concentration became equal to 1%. Compounds were dispensed in triplicate in assay plates (4 µl). Total binding and nonspecific binding wells were set up in 6 wells as vehicle and 10 µM dofetilide at final concentration, respectively. The radioligand was prepared at 5.6× final concentration and this solution was added to each well (36 µl). The assay was initiated by addition of YSi poly-L-lysine SPA beads (50 µl, 1 mg/well) and membranes (110 µl, 20 µg/well). Incubation was continued for 60 min at room temperature. Plates were incubated for a further 3 hours at room temperature for beads to settle. Receptor-bound radioactivity was quantified by counting Wallac MicroBeta plate counter.

$I_{HERG}$ Assay

HEK 293 cells which stably express the HERG potassium channel were used for electrophysiological study. The methodology for stable transfection of this channel in HEK cells can be found elsewhere (Z. Zhou et al., 1998, Biophysical Journal, 74, pp 230-241). Before the day of experimentation, the cells were harvested from culture flasks and plated onto glass coverslips in a standard MEM medium with 10% FCS. The plated cells were stored in an incubator at 37° C. maintained in an atmosphere of 95% $O_2$/5% $CO_2$. Cells were studied between 15-28 hrs after harvest.

HERG currents were studied using standard patch clamp techniques in the whole-cell mode. During the experiment the cells were superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings was made using a patch clamp amplifier and patch pipettes which have a resistance of 1-3 MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15 MΩ and seal resistances >1 GΩ was accepted for further experimentation. Series resistance compensation was applied up to a maximum of 80%. No leak subtraction was done. However, acceptable access resistance depended on the size of the recorded currents and the level of series resistance compensation that can safely be used. Following the achievement of whole cell configuration and sufficient time for cell dialysis with pipette solution (>5 min), a standard voltage protocol was applied to the cell to evoke membrane currents. The voltage protocol is as follows. The membrane was depolarized from a holding potential of −80 mV to +40 mV for 1000 ms. This was followed by a descending voltage ramp (rate 0.5 mV $msec^{-1}$) back to the holding potential. The voltage protocol was applied to a cell continuously throughout the experiment every 4 seconds (0.25 Hz). The amplitude of the peak current elicited around −40 mV during the ramp was measured. Once stable evoked current responses were obtained in the external solution, vehicle (0.5% DMSO in the standard external solution) was applied for 10-20 min by a peristalic pump. Provided there were minimal changes in the amplitude of the evoked current response in the vehicle control condition, the test compound of either 0.3, 1, 3, 10 μM was applied for a 10 min period. The 10 min period included the time which supplying solution was passing through the tube from solution reservoir to the recording chamber via the pump. Exposing time of cells to the compound solution was more than 5 min after the drug concentration in the chamber well reached the attempting concentration. There was a subsequent wash period of a 10-20 min to assess reversibility. Finally, the cells was exposed to high dose of dofetilide (5 μM), a specific IKr blocker, to evaluate the insensitive endogenous current.

All experiments were performed at room temperature (23±1° C.). Evoked membrane currents were recorded on-line on a computer, filtered at 500-1 KHz (Bessel −3 dB) and sampled at 1-2 KHz using the patch clamp amplifier and a specific data analyzing software. Peak current amplitude, which occurred at around −40 mV, was measured off line on the computer.

The arithmetic mean of the ten values of amplitude was calculated under vehicle control conditions and in the presence of drug. Percent decrease of $I_N$ in each experiment was obtained by the normalized current value using the following formula: $I_N=(1-I_D/I_C)\times100$, where $I_D$ is the mean current value in the presence of drug and $I_C$ is the mean current value under control conditions. Separate experiments were performed for each drug concentration or time-matched control, and arithmetic mean in each experiment is defined as the result of the study.

Drug-Drug Interaction Assay

This method essentially involves determining the percent inhibition of product formation from fluorescence probe at 3 μM of the each compound.

More specifically, the assay is carried out as follows. The compounds were pre-incubated with recombinant CYPs, 100 mM potassium phosphate buffer and fluorescence probe as substrate for 5 min. Reaction was started by adding a warmed NADPH generating system, which consist of 0.5 mM NADP (expect; for 2D6 0.03 mM), 10 mM $MgCl_2$, 6.2 mM DL-Isocitric acid and 0.5 U/ml Isocitric Dehydrogenase (ICD). The assay plate was incubated at 37° C. (expect; for 1A2 and 3A4 at 30° C.) and taking fluoresce reading every minutes over 20 to 30 min.

Data calculations were preceded as follows;
1. The slope (Time vs. Fluorescence units) was calculated at the linear region
2. The percentage of inhibition in compounds was calculated by the equation $$\{(v_o-v_i)/v_o\}\times100=\% \text{ inhibition}$$

Wherein
$v_o$=rate of control reaction (no inhibitor)
$v_i$=rate of reaction in the presence of compounds.

TABLE 1

Condition for drug-drug interaction assay.

|  | 1A2 | 2C9 | 2C19 | 2D6 | 3A4 |
|---|---|---|---|---|---|
| Substrate | Vivid blue (Aurora) | MFC (Gentest) | Vivid blue (Aurora) | AMMC (Gentest) | Vivid red (Aurora) |
| Substrate (μM) | 10 | 30 | 10 | 1 | 2 |
| Enzyme (pmol) | 50 | 50 | 5 | 50 | 5 |
| EX./Em(λ) | 408/465 | 408/535 | 408/465 | 400/465 | 530/595 |

Half-Life in Human Liver Microsomes (HLM)

Test compounds (1 μM) were incubated with 3.3 mM $MgCl_2$ and 0.78 mg/mL HLM (HL101) in 100 mM potassium phosphate buffer (pH 7.4) at 37° C. on the 96-deep well plate. The reaction mixture was split into two groups, a non-P450 and a P450 group. NADPH was only added to the reaction mixture of the P450 group. An aliquot of samples of P450 group was collected at 0, 10, 30, and 60 min time point, where 0 min time point indicated the time when NADPH was added into the reaction mixture of P450 group. An aliquot of samples of non-P450 group was collected at −10 and 65 min time point. Collected aliquots were extracted with acetonitrile solution containing an internal standard. The precipitated protein was spun down in centrifuge (2000 rpm, 15 min). The compound concentration in supernatant was measured by LC/MS/MS system.

The half-life value was obtained by plotting the natural logarithm of the peak area ratio of compounds/internal standard versus time. The slope of the line of best fit through the points yields the rate of metabolism (k). This was converted to a half-life value using following equations:

$$\text{Half-life}=\ln2/k$$

Pharmaceutically acceptable salts of the compounds of formula (I) include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002). A pharmaceutically acceptable salt of a compound of formula (I) may be readily prepared by mixing together solutions of the compound of formula (I) and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised.

For a review of such complexes, see J Pharm Sci, 64 (8), 1269-1288 by Haleblian (August 1975).

Hereinafter all references to compounds of formula (I) include references to salts, solvates and complexes thereof and to solvates and complexes of salts thereof.

The compounds of the invention include compounds of formula (I) as hereinbefore defined, polymorphs, prodrugs, and isomers thereof (including optical, geometric and tautomeric isomers) as hereinafter defined and isotopically-labeled compounds of formula (I).

As stated, the invention includes all polymorphs of the compounds of formula (I) as hereinbefore defined.

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985).

Some examples of prodrugs in accordance with the invention include:

(i) where the compound of formula (I) contains a carboxylic acid functionality (—COOH), an ester thereof, for example, replacement of the hydrogen with $(C_1-C_8)$alkyl;

(ii) where the compound of formula (I) contains an alcohol functionality (—OH), an ether thereof, for example, replacement of the hydrogen with $(C_1-C_6)$alkanoyloxymethyl; and (iii) where the compound of formula (I) contains a primary or secondary amino functionality (—$NH_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I). Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism. Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine. Cis/trans isomers may be separated by conventional techniques well known to those skilled in the art, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomeric conglomerates may be separated by conventional techniques known to those skilled in the art—see, for example, "Stereochemistry of Organic Compounds" by E L Eliel (Wiley, New York, 1994). The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

The compounds of the invention may be administered in combination, separately, simultaneously or sequentially, with one or more other pharmacologically active agents. Suitable agents, particularly for the treatment of pain, include:

(i) opioid analgesics, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine and pentazocine;

(ii) nonsteroidal antiinflammatory drugs (NSAIDs), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, and their pharmaceutically acceptable salts;

(iii) barbiturate sedatives, e.g. amobarbital, aprobarbital, butabarbital, butabital, mephobarbital, metharbital, methohexital, pentobarbital, phenobartital, secobarbital, talbutal, theamylal, thiopental and their pharmaceutically acceptable salts;

(iv) benzodiazepines having a sedative action, e.g. chlordiazepoxide, clorazepate, diazepam, flurazepam, lorazepam, oxazepam, temazepam, triazolam and their pharmaceutically acceptable salts, (v) $H_1$ antagonists having a sedative action, e.g. diphenhydramine, pyrilamine, promethazine, chlorpheniramine, chlorcyclizine and their pharmaceutically acceptable salts;

(vi) miscellaneous sedatives such as glutethimide, meprobamate, methaqualone, dichloralphenazone and their pharmaceutically acceptable salts;

(vii) skeletal muscle relaxants, e.g. baclofen, carisoprodol, chlorzoxazone, cyclobenzaprine, methocarbamol, orphrenadine and their pharmaceutically acceptable salts, (viii) alpha-2-delta ligands, e.g. gabapentin and pregabalin;

(ix) alpha-adrenergic active compounds, e.g. doxazosin, tamsulosin, clonidine and 4-amino-6,7-dimethoxy-2-(5-methanesulfonamido-1,2,3,4-tetrahydroisoquinol-2-yl)-5-(2-pyridyl) quinazoline;

(x) tricyclic antidepressants, e.g. desipramine, imipramine, amytriptiline and nortriptiline;

(xi) anticonvulsants, e.g. carbamazepine and valproate;

(xii) serotonin reuptake inhibitors, e.g. fluoxetine, paroxetine, citalopram and sertraline;

(xiii) mixed serotonin-noradrenaline reuptake inhibitors, e.g. milnacipran, venlafaxine and duloxetine;

(xiv) noradrenaline reuptake inhibitors, e.g. reboxetine;

(xv) Tachykinin (NK) antagonists, particularly NK-3, NK-2 and NK-1 antagonists, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis (trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S)

(xvi) Muscarinic antagonists, e.g oxybutin, tolterodine, propiverine, tropsium chloride and darifenacin;

(xvii) COX-2 inhibitors, e.g. celecoxib, rofecoxib and valdecoxib;

(xviii) Non-selective COX inhibitors (preferably with GI protection), e.g. nitroflurbiprofen (HCT-1026);

(xix) coal-tar analgesics, in particular, paracetamol;

(xx) neuroleptics, such as droperidol;

(xxi) Vanilloid receptor agonists, e.g. resinferatoxin;

(xxii) Beta-adrenergic compounds such as propranolol;

(xxiii) Local anaesthetics, such as mexiletine;

(xxiv) Corticosteriods, such as dexamethasone (xxv) serotonin receptor agonists and antagonists;

(xxvi) cholinergic (nicotinic) analgesics; and (xxvii) miscellaneous analgesic agents, such as Tramadol®.

(xxviii) NMDA receptor antagonists, e.g. dextromethorphan ((+)-3-hydroxy-N-methylmorphinan) and its metabolite dextrorphan ((+)-3-hydroxy-N-methylmorphinan), ketamine, memantine, pyrroloquinoline quinone and cis-4-(phosphonomethyl)-2-piperidinecarboxylic acid and their pharmaceutically acceptable salts;

(xxix) PDEV inhibitors, such as sildenafil, vardenafil or taladafil.

Thus, the invention further provides a combination comprising a compound of the invention or a pharmaceutically acceptable salt, solvate or pro-drug thereof, and a compound or class of compounds selected from the group (i)-(xxix), above. There is also provided a pharmaceutical composition comprising such a combination, together with a pharmaceutically acceptable excipient, diluent or carrier, particularly for the treatment of a disease for which an EP4 antagonist is implicated.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

Oral Administration

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified controlled release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably. to a pH of from 3 to 9), but, for some applications, they may be more suitably formulated as a sterile non-aqueous solution or as powdered a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents. Formulations for use with needle-free injection administration comprise a compound of the invention in powdered form in conjunction with a suitable vehicle such as sterile, pyrogen-free water.

Formulations for parenteral administration may be formulated to be immediate and/or modified controlled release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose tio include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999). Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified controlled release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified controlled release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 µg to 10 mg of the compound of formula (I). The overall daily dose will typically be in the range 1 µg to 10 mg which may be administered in a single dose or, more usually, as divided doses throughout the day.

Rectal/Intravaginal Administration

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified controlled release. Modified release formulations include delayed-, sustained-, pulsed-, controlled-, targeted and programmed release.

Ocular/Aural Administration

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified controlled release. Modified release formulations include delayed-, sustained-, pulsed-, controlled-, targeted, or programmed release.

Other Technologies

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Kit-of-Parts

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

Dosage

For administration to human patients, the total daily dose of the compounds of the invention is typically in the range 0.1 mg to 3000 mg, preferably from 1 mg to 500 mg, depending, of course, on the mode of administration. For example, oral administration may require a total daily dose of from 0.1 mg to 3000 mg, preferably from 1 mg to 500 mg, while an intravenous dose may only require from 0.1 mg to 1000 mg, preferably from 0.1 mg to 300 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

EXAMPLES

The invention is illustrated in the following non-limiting examples in which, unless stated otherwise: all operations were carried out at room or ambient temperature, that is, in the range of 18-25° C.; evaporation of solvent was carried out using a rotary evaporator under reduced pressure with a bath temperature of up to 60° C.; reactions were monitored by thin layer chromatography (TLC); melting points (mp) given are uncorrected; the structure and purity of all isolated compounds were assured by at least one of the following techniques: TLC (Merck silica gel 60 $F_{254}$ precoated TLC plates or Merck $NH_2$ gel (an amine coated silica gel) $F_{254s}$ precoated TLC plates), mass spectrometry, nuclear magnetic resonance spectra (NMR), infrared absorption spectra (IR) or microanalysis. Yields are given for illustrative purposes only. Workup with a cation-exchange column was carried out using SCX cartridge (Varian BondElute), which was preconditioned with methanol. Flash column chromatography was carried out using Merck silica gel 60 (63-200 µm), Wako silica gel 300HG (40-60 µm), Fuji Silysia NH gel (an amine coated silica gel) (30-50 µm), Biotage KP-SIL (32-63 µm) or Biotage AMINOSILICA (an amine coated silica gel) (40-75 µm). Preparative TLC was carried out using Merck silica gel 60 $F_{254}$ precoated TLC plates (0.5 or 1.0 mm thickness). Low-resolution mass spectral data (EI) were obtained on an Integrity (Waters) mass spectrometer. Low-resolution mass spectral data (ESI) were obtained on a ZMD (Micromass) mass spectrometer. NMR data was determined at 270 MHz (JEOL JNM-LA 270 spectrometer), 300 MHz (JEOL JNM-LA300 spectrometer) or 600 MHz (Bruker AVANCE 600 spectrometer) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, quint=quintet, m=multiplet, br.=broad, etc. IR spectra were measured by a Shimazu infrared spectrometer (IR-470). Chemical symbols have their usual meanings; bp (boiling point), mp (melting point), L (liter(s)), mL (milliliter(s)), g (gram(s)), mg (milligram(s)), mol (moles), mmol (millimoles), eq. (equivalent(s)), quant. (quantitative yield).

Example 1

4-[(1S)-1-({5-chloro-2-[(2-chlorophenoxy)methyl]benzoyl}amino)ethyl]benzoic Acid

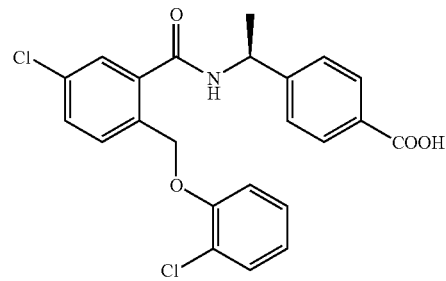

STEP 1. Methyl 5-chloro-2-[(2-chlorophenoxy)methyl]benzoate

A mixture of methyl 2-(bromoethyl)-5-chlorobenzoate (100 mg, 0.38 mmol), 2-chlorophenol (43 µL, 0.42 mmol) and potassium carbonate (105 mg, 0.76 mmol) in N,N-dimethylformamide (2 mL) was stirred at room temperature for 3 h and at 50° C. for 4 hours. Water (5 mL) was added and the mixture was extracted with diethyl ether (15 mL×2). The combined organic extracts were washed with brine (15 mL) and dried (sodium sulfate). After removal of solvent, the residue was purified by pTLC eluting with hexane/ethyl acetate (9/1) to afford 103 mg (87%) of the title compound:

$^1$H-NMR (CDCl$_3$) δ 8.04-8.03 (1H, m), 7.91-7.87 (1H, m), 7.59-7.55 (1H, m), 7.42-7.39 (1H, m), 7.24-7.18 (1H, m), 7.02-6.90 (2H, m), 5.53 (2H, s), 3.93 (3H, s).

STEP 2. 5-Chloro-2-[(2-chlorophenoxy)methyl]benzoic acid

To a solution of methyl 5-chloro-2-[(2-chlorophenoxy)methyl]benzoate (step 1, 103 mg, 0.33 mmol) in methanol (4 mL) and tetrahydrofuran (4 mL) was 2 N sodium hydroxide (1 mL) and the mixture was stirred at room temperature for 16 hours. After removal of solvent, the residue was diluted with water (5 mL) and the solution was acidified with 2 N hydrochloric acid. Precipitate was collected by filtration, washed with water and dried in vacuo to afford 85 mg (86%) of the title compound:

$^1$H-NMR (DMSO-d$_6$) δ 7.92 (1H, br.s), 7.33 (2H, br.s), 7.48-7.45 (1H, m), 7.35-7.28 (1H, m), 7.15-7.12 (1H, m), 7.02-6.96 (1H, m), 5.52 (2H, s), A peak of COOH was not observed;

MS (ESI) m/z 295 (M−H)$^-$.

STEP 3. tert-Butyl [(1S)-1-(4-bromophenyl)ethyl]carbamate

A mixture of [(1S)-1-(4-bromophenyl)ethyl]amine (10.00 g, 50.0 mmol) and di-tert-butyl dicarbonate (11.45 g, 52.5 mmol), triethylamine (7.66 mL, 55.0 mmol) in dichloromethane (200 mL) was stirred at room temperature for 1 hour. The mixture was diluted with dichloromethane (500 mL) and washed with 1 M hydrochloric acid (300 mL), saturated sodium hydrogen carbonate aqueous (300 mL), and brine (300 mL). The organic layer was dried over magnesium sulfate, and concentrated under reduced pressure. The residue was washed with cold hexane to afford 14.73 g (98%) of the title compound as white solids:

$^1$H-NMR (CDCl$_3$) δ 7.47-7.42 (2H, m), 7.18 (2H, d, J=8.4 Hz), 5.30 (2H, br.s), 1.41 (12H, br.s)

STEP 4. Methyl 4-{(1S)-1-[(tert-butoxycarbonyl)amino]ethyl}benzoate

A mixture of tert-butyl [(1S)-1-(4-bromophenyl)ethyl]carbamate (step 3, 14.73 g, 49.1 mmol), 1,3-bis(diphenylphosphino)-propane (2.03 g, 4.91 mmol), palladium (II) acetate (1.10 g, 4.91 mmol), triethylamine (20.5 mL, 147 mmol), N,N-dimethylforamide (120 mL) and methanol (180 mL) was stirred at 80° C. for 16 h under carbon monoxide atmosphere. After cooling to room temperature, the mixture was diluted with ether (800 mL) and washed with water (500 mL×3). The organic layer was dried over magnesium sulfate and evaporated. The residue was purified by flush column chromatography on silica gel eluting with hexane/ethyl acetate (5:1) to afford 12.83 g (94%) of the title compound as white solids:

$^1$H-NMR (CDCl$_3$) δ 8.02-7.99 (2H, m), 7.37 (2H, d, J=8.4 Hz), 4.83 (2H, br.s), 3.91 (3H, s), 1.46-1.42 (12H, m)

STEP 5. Methyl 4-[(1S)-1-aminoethyl]benzoate hydrochloride

Methyl 4-{(1S)-1-[(tert-butoxycarbonyl)amino]ethyl}benzoate (step 4, 12.83 g, 45.9 mmol) was treated with trifluoroacetic acid (100 mL) and dichloromethane (100 mL) at room temperature for 16 hours. After removal of the solvent, the residue was diluted with 10% hydrogen chloride solution in methanol (100 mL). The mixture was concentrated under reduced pressure and the residue was washed with ethylacetate to give 9.40 g (95%) of the title compound as white solids:

$^1$H-NMR (DMSO-d$_6$) δ 8.67 (2H, br.s), 8.01 (2H, d, J=8.4 Hz), 7.68 (2H, d, J=8.4 Hz), 4.49 (1H, q, J=6.9 Hz), 3.87 (3H, s), 1.53 (3H, d, J=6.9 Hz)

STEP 6. Methyl 4-[(1S)-1-({5-chloro-2-[(2-chlorophenoxy)methyl]benzoyl}amino) ethyl]benzoate A mixture of 5-chloro-2-[(2-chlorophenoxy)methyl]benzoic acid (step 2, 85 mg, 0.28 mmol), methyl 4-[(1S)-1-aminoethyl]benzoate hydrochloride (step 5, 73 mg, 0.34 mmol), 1-(3-dimethylaminopropyl)-3-ethylcarbodiimide hydrochloride (EDCI) (107 mg, 0.56 mmol), 1-hydroxybenzotriazole hydrate (HOBT) (76 mg, 0.56 mmol) and triethylamine (117 μL, 0.84 mmol) in dichloromethane (3 mL) was stirred at room temperature for 19 hours. Water (5 mL) was added and the organic phase was separated. The aqueous phase was extracted with ethyl acetate (10 mL×2) and the combined organic extracts were dried (sodium sulfate). After removal of solvent, the residue was purified by pTLC eluting with hexane/ethyl acetate (2/1) to afford 105 mg (82%) of the title compound:

$^1$H-NMR (CDCl$_3$) δ 7.90-7.87 (2H, m), 7.64 (1H, d, J=2.2 Hz), 7.50-7.31 (5H, m), 7.24-7.18 (1H, m), 6.97-6.87 (3H, m). 5.36-5.25 (1H, m), 5.06 (2H, dd, J=19.6, 11.2 Hz), 3.91 (3H, s), 1.27 (3H, d, J=7.3 Hz);

MS (ESI) m/z 458 (M+H)$^+$, 456 (M–H)$^-$.

STEP 7. 4-[(1S)-1-({5-Chloro-2-[(2-chlorophenoxy)methyl]benzoyl}amino)ethyl]benzoic acid To a stirred solution of methyl 4-[(1S)-1-({5-chloro-2-[(2-chlorophenoxy)methyl]benzoyl}amino)ethyl]benzoate (step 6, 407 mg, 1.02 mmol) in methanol (10 ml) was added 2 N sodium hydroxide aqueous solution (2 ml). The reaction mixture was stirred at room temperature for 3 h and then evaporated. The residue was partitioned between ethyl acetate (100 mL) and 2 N hydrochloric acid (100 mL). The organic phase was separated and the aqueous phase was extracted with ethyl acetate (100 mL). The combined organic extracts were washed with brine (50 mL), dried (sodium sulfate), and concentrated. The residual solids were recrystallized from ethyl acetate to afford 248 mg (64%) of the title compound as white solids:

$^1$H-NMR (DMSO-d$_6$) δ 9.10-9.07 (1H, m), 7.87-7.84 (2H, m), 7.67-7.59 (3H, m), 7.48-7.42 (3H, m), 7.29-7.23 (1H, m), 7.03-6.94 (2H, m), 5.23 (1H, s), 5.17-5.06 (1H, m), 1.44 (3H, d, J=7.0 Hz), A peak of COOH was not observed;

MS (ESI) m/z 444 (M+H)$^+$, 442 (M–H)$^-$.

Example 2

4-[(1S)-1-({5-chloro-2-[(3-chlorophenoxy)methyl]benzoyl}amino)ethyl]benzoic Acid

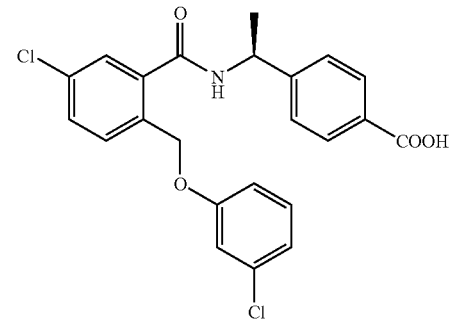

STEP 1. Methyl 5-chloro-2-[(3-chlorophenoxy)methyl]benzoate

The title compound was prepared according to the procedure described in step 1 of Example 1 from methyl 2-(bromoethyl)-5-chlorobenzoate and 3-chlorophenol:

$^1$H-NMR (CDCl$_3$) δ 8.02 (1H, d, J=2.4 Hz), 7.67 (1H, d, J=8.4 Hz), 7.53 (1H, dd, J=8.4, 2.4 Hz), 7.21 (1H, t, J=8.1 Hz), 7.00-6.85 (3H, m), 5.44 (2H, s), 3.92 (3H, s).

STEP 2. 5-Chloro-2-[(3-chlorophenoxy)methyl]benzoic acid

The title compound was prepared according to the procedure described in step 2 of Example 1 from methyl 5-chloro-2-[(3-chlorophenoxy)methyl]benzoate (step 1):

$^1$H-NMR (DMSO-d$_6$) δ 7.90-7.89 (1H, m), 7.70-7.62 (2H, m), 7.36-7.30 (1H, m), 7.08-6.74 (3H, m), 5.44 (2H, s), a peak of COOH was not observed;

MS (ESI) m/z 295 (M–H)$^-$.

STEP 3. Methyl 4-[(1S)-1-({5-chloro-2-[(3-chlorophenoxy)methyl]benzoyl}amino)ethyl]benzoate The title compound was prepared according to the procedure described in step 6 of Example 1 from 5-chloro-2-[(3-chlorophenoxy)methyl]benzoic acid (step 2) and methyl 4-[(1S)-1-aminoethyl]benzoate hydrochloride (step 5 of Example 1):

$^1$H-NMR (CDCl$_3$) δ 7.93-7.90 (2H, m), 7.61 (1H, br.s), 7.45-7.44 (2H, m), 7.33-7.30 (2H, m), 7.22-7.16 (1H, m). 6.99-6.96 (1H, m), 6.85-6.84 (1H, m), 6.77-6.73 (1H, m), 6.66-6.63 (1H, m), 5.34-5.23 (1H, m), 5.02 (2H, s), 3.92 (3H, s), 1.49 (3H, d, J=7.0 Hz);
MS (ESI) m/z 458 (M+H)$^+$, 456 (M−H)$^−$.

STEP 4. 4-[(1S)-1-({5-Chloro-2-[(3-chlorophenoxy)methyl]benzoyl}amino)ethyl]benzoic acid The title compound was prepared according to the procedure described in step 7 of Example 1 from methyl 4-[(1S)-1-({5-chloro-2-[(3-chlorophenoxy)methyl]benzoyl}amino)ethyl]benzoate (step 3):

$^1$H-NMR (DMSO-d$_6$) δ 9.05-9.02 (1H, m), 7.82-7.85 (2H, m), 7.61-7.55 (3H, m), 7.42-7.39 (2H, m), 7.30-7.24 (1H, m), 7.01-6.94 (2H, m), 6.83-6.79 (1H, m), 5.17 (2H, s), 5.15-5.05 (1H, m), 1.42 (3H, d, J=7.3 Hz), a peak of COOH was not observed;
MS (ESI) m/z 444 (M+H)$^+$, 442 (M−H)$^−$.

Example 3

4-[(1S)-1-({5-chloro-2-[(4-chlorophenoxy)methyl]benzoyl}amino)ethyl]benzoic Acid

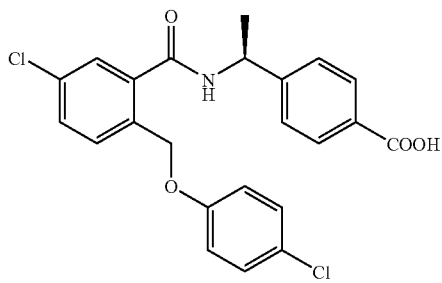

STEP 1. Methyl 5-chloro-2-[(4-chlorophenoxy)methyl]benzoate

The title compound was prepared according to the procedure described in step 1 of Example 1 from methyl 2-(bromoethyl)-5-chlorobenzoate and 4-chlorophenol:

$^1$H-NMR (CDCl$_3$) δ 8.02 (1H, d, J=2.3 Hz), 7.68 (1H, d, J=8.5 Hz), 7.52 (1H, dd, J=8.5, 2.3 Hz), 7.28-7.22 (2H, m), 6.94-6.88 (2H, m), 5.43 (2H, s), 3.91 (3H, s).

STEP 2. 5-Chloro-2-[(4-chlorophenoxy)methyl]benzoic acid

The title compound was prepared according to the procedure described in step 2 of Example 1 from methyl 5-chloro-2-[(4-chlorophenoxy)methyl]benzoate (step 1):

$^1$H-NMR (DMSO-d$_6$) δ 7.89-7.88 (1H, m), 7.69-7.61 (2H, m), 7.38-7.32 (2H, m), 7.03-6.97 (2H, m), 5.42 (2H, s), A peak of COOH was not observed;
MS (ESI) m/z 295 (M−H)$^−$.

STEP 3. Methyl 4-[(1S)-1-({5-chloro-2-[(4-chlorophenoxy)methyl]benzoyl}amino)ethyl]benzoate The title compound was prepared according to the procedure described in step 6 of Example 1 from 5-chloro-2-[(4-chlorophenoxy)methyl]benzoic acid (step 2) and methyl 4-[(1S)-1-aminoethyl]benzoate hydrochloride (step 5 of Example 1):

$^1$H-NMR (CDCl$_3$) δ 7.91-7.88 (2H, m), 7.62 (1H, br.s), 7.44 (2H, br.s), 7.37-7.19 (4H, m), 6.82-6.74 (2H, m), 6.67-6.39 (1H, m), 5.34-5.23 (1H, m), 5.00 (2H, s), 3.92 (3H, s), 1.48 (3H, d, J=6.8 Hz);
MS (ESI) m/z 458 (M+H)$^+$, 456 (M−H)$^−$.

STEP 4. 4-[(1S)-1-({5-Chloro-2-[(4-chlorophenoxy)methyl]benzoyl}amino)ethyl]benzoic acid The title compound was prepared according to the procedure described in step 7 of Example 1 from methyl 4-[(1S)-1-({5-chloro-2-[(4-chlorophenoxy)methyl]benzoyl}amino)ethyl]benzoate (step 3):

$^1$H-NMR (DMSO-d$_6$) δ 9.07-9.04 (1H, m), 7.87-7.84 (2H, m), 7.60-7.54 (3H, m), 7.48-7.45 (2H, m), 7.29-7.26 (2H, m), 6.87-6.84 (2H, m), 5.17-5.05 (3H, m), 1.43 (3H, d, J=7.0 Hz), a peak of COOH was not observed;
MS (ESI) m/z 444 (M+H)$^+$, 442 (M−H)$^−$.

Example 4

4-[(1S)-1-({5-chloro-2-[(4-fluorophenoxy)methyl]benzoyl}amino)ethyl]benzoic Acid

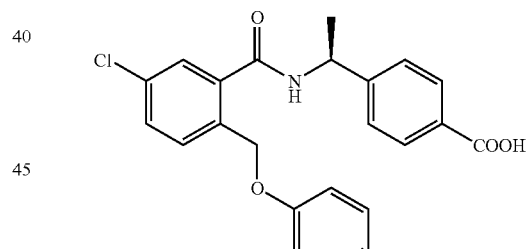

STEP 1. Methyl 5-chloro-2-[(4-fluorophenoxy)methyl]benzoate

The title compound was prepared according to the procedure described in step 1 of Example 1 from methyl 2-(bromoethyl)-5-chlorobenzoate and 4-fluorophenol:

$^1$H-NMR (CDCl$_3$) δ 8.01 (1H, d, J=2.2 Hz), 7.69 (1H, d, J=8.5 Hz), 7.52 (1H, dd, J=8.5, 2.2 Hz), 7.02-6.89 (4H, m), 5.42 (2H, s), 3.91 (3H, s).

STEP 2. 5-Chloro-2-[(4-fluorophenoxy)methyl]benzoic acid

The title compound was prepared according to the procedure described in step 2 of Example 1 from methyl 5-chloro-2-[(4-fluorophenoxy)methyl]benzoate (step 1):

$^1$H-NMR (DMSO-d$_6$) δ 7.90-7.89 (1H, m), 7.71-7.63 (2H, m), 7.17-7.10 (2H, m), 7.01-6.96 (2H, m), 5.40 (2H, s), a peak of COOH was not observed;
MS (ESI) m/z 279 (M−H)$^-$.

STEP 3. Methyl 4-[(1S)-1-({5-chloro-2-[(4-fluorophenoxy)methyl]benzoyl}amino)ethyl]benzoate The title compound was prepared according to the procedure described in step 6 of Example 1 from 5-chloro-2-[(4-fluorophenoxy)methyl]benzoic acid (step 2) and methyl 4-[(1S)-1-aminoethyl]benzoate hydrochloride (step 5 of Example 1):
$^1$H-NMR (CDCl$_3$) δ7.91-7.88 (2H, m), 7.63 (1H, br.s), 7.47-7.40 (2H, m), 7.32-7.29 (2H, m), 6.99-6.92 (2H, m), 6.81-6.75 (3H, m), 5.33-5.23 (1H, m), 4.98 (2H, s), 3.92 (3H, s), 1.47 (3H, d, J=7.0 Hz);
MS (ESI) m/z 442 (M+H)$^+$, 440 (M−H)$^-$.

STEP 4. 4-[(1S)-1-({5-Chloro-2-[(4-fluorophenoxy)methyl]benzoyl}amino)ethyl]benzoic acid The title compound was prepared according to the procedure described in step 7 of Example 1 from methyl 4-[(1S)-1-({5-chloro-2-[(4-fluorophenoxy)methyl]benzoyl}amino)ethyl]benzoate (step 3):
$^1$H-NMR (DMSO-d$_6$) δ 9.07-9.04 (1H, m), 7.86-7.83 (2H, m), 7.61-7.54 (3H, m), 7.49-7.46 (2H, m), 7.10-7.03 (2H, m), 6.88-6.82 (2H, m), 5.13-5.05 (3H, m), 1.42 (3H, d, J=6.8 Hz), a peak of COOH was not observed;
MS (ESI) m/z 428 (M+H)$^+$, 426 (M−H)$^-$.

Example 5

4-[(1S)-1-({5-chloro-2-[(3-fluorophenoxy)methyl]benzoyl}amino)ethyl]benzoic Acid

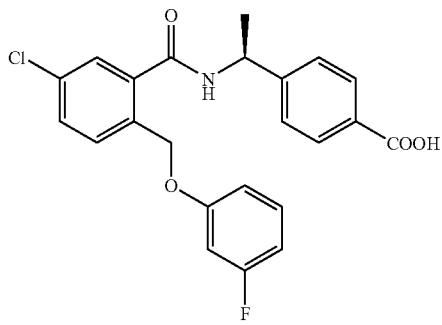

STEP 1. Methyl 5-chloro-2-[(3-fluorophenoxy)methyl]benzoate

The title compound was prepared according to the procedure described in step 1 of Example 1 from methyl 2-(bromoethyl)-5-chlorobenzoate and 3-fluorophenol:
$^1$H-NMR (CDCl$_3$) δ 8.02 (1H, d, J=2.3 Hz), 7.68 (1H, d, J=8.6 Hz), 7.53 (1H, dd, J=8.6, 2.3 Hz), 7.28-7.19 (1H, m), 6.78-6.65 (3H, m), 5.45 (2H, s), 3.92 (3H, s).

STEP 2. 5-Chloro-2-[(3-fluorophenoxy)methyl]benzoic acid

The title compound was prepared according to the procedure described in step 2 of Example 1 from methyl 5-chloro-2-[(3-fluorophenoxy)methyl]benzoate (step 1):

$^1$H-NMR (DMSO-d$_6$) δ 7.91-7.89 (1H, m), 7.71-7.63 (2H, m), 7.38-7.29 (1H, m), 6.89-6.75 (3H, m), 5.44 (2H, s), a peak of COOH was not observed.

STEP 3. Methyl 4-[(1S)-1-({5-chloro-2-[(3-fluorophenoxy)methyl]benzoyl}amino)ethyl]benzoate The title compound was prepared according to the procedure described in step 6 of Example 1 from 5-chloro-2-[(3-fluorophenoxy)methyl]benzoic acid (step 2) and methyl 4-[(1S)-1-aminoethyl]benzoate hydrochloride (step 5 of Example 1):
$^1$H-NMR (CDCl$_3$) δ 7.93-7.90 (2H, m), 7.61 (1H, br.s), 7.45 (2H, br.s), 7.33-7.18 (3H, m), 6.75-6.54 (4H, m), 5.31-5.26 (1H, m), 5.03 (2H, s), 3.91 (3H, s), 1.48 (3H, d, J=7.1 Hz);
MS (ESI) m/z 442 (M+H)$^+$.

STEP 4. 4-[(1S)-1-({5-Chloro-2-[(3-fluorophenoxy)methyl]benzoyl}amino)ethyl]benzoic acid The title compound was prepared according to the procedure described in step 7 of Example 1 from methyl 4-[(1S)-1-({5-chloro-2-[(3-fluorophenoxy)methyl]benzoyl}amino)ethyl]benzoate (step 3):
$^1$H-NMR (DMSO-d$_6$) δ 9.08-9.05 (1H, m), 7.87-7.84 (2H, m), 7.61-7.55 (3H, m), 7.49-7.46 (2H, m), 7.31-7.23 (1H, m), 6.79-6.67 (3H, m), 5.20-5.06 (3H, m), 1.43 (3H, d, J=7.0 Hz), a peak of COOH was not observed;
MS (ESI) m/z 428 (M+H)$^+$, 426 (M−H)$^-$.

Example 6

4-[(1S)-1-({5-chloro-2-[(2-fluorophenoxy)methyl]benzoyl}amino)ethyl]benzoic Acid

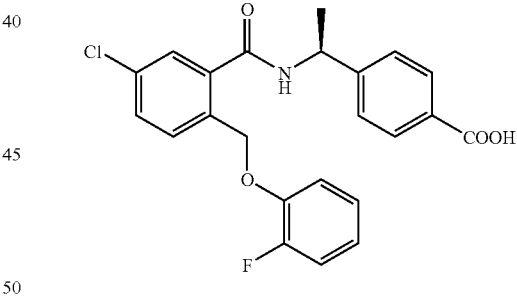

STEP 1. Methyl 5-chloro-2-[(2-fluorophenoxy)methyl]benzoate

The title compound was prepared according to the procedure described in step 1 of Example 1 from methyl 2-(bromoethyl)-5-chlorobenzoate and 2-fluorophenol: $^1$H-NMR (CDCl$_3$) δ 8.02 (1H, d, J=2.4 Hz), 7.80-7.77 (1H, m), 7.57-7.53 (1H, m), 7.15-6.89 (4H, m), 5.52 (2H, s), 3.92 (3H, s).

STEP 2. 5-Chloro-2-[(3-fluorophenoxy)methyl]benzoic acid

The title compound was prepared according to the procedure described in step 2 of Example 1 from methyl 5-chloro-2-[(2-fluorophenoxy)methyl]benzoate (step 1):

¹H-NMR (DMSO-d₆) δ 7.91-7.90 (1H, m), 7.74-7.66 (2H, m), 7.28-7.09 (3H, m), 7.01-6.93 (1H, m), 5.49 (2H, s), a peak of COOH was not observed.

STEP 3. Methyl 4-[(1S)-1-({5-chloro-2-[(2-fluorophenoxy)methyl]benzoyl}amino)ethyl]benzoate The title compound was prepared according to the procedure described in step 6 of Example 1 from 5-chloro-2-[(2-fluorophenoxy)methyl]benzoic acid (step 2) and methyl 4-[(1S)-1-aminoethyl]benzoate hydrochloride (step 5 of Example 1):

¹H-NMR (CDCl₃) δ 7.91 (2H, d, J=8.2 Hz), 7.63 (1H, br.s), 7.42 (2H, br.s), 7.35 (2H, d, J=8.2 Hz), 7.11-6.89 (5H, m), 5.35-5.24 (1H, m), 5.15-5.05 (2H, m), 3.91 (3H, s), 1.50 (3H, d, J=6.9 Hz);

MS (ESI) m/z 442 (M+H)⁺.

STEP 4. 4-[(1S)-1-({5-Chloro-2-[(2-fluorophenoxy)methyl]benzoyl}amino)ethyl]benzoic acid The title compound was prepared according to the procedure described in step 7 of Example 1 from methyl 4-[(1S)-1-({5-chloro-2-[(2-fluorophenoxy)methyl]benzoyl}amino)ethyl]benzoate (step 3):

¹H-NMR (DMSO-d₆) δ 9.11-9.08 (1H, m), 7.86-7.83 (2H, m), 7.64-7.57 (3H, m), 7.49-7.46 (2H, m), 7.25-7.17 (1H, m), 7.11-7.03 (2H, m), 6.98-6.90 (1H, m), 5.21-5.05 (3H, m), 1.43 (3H, d, J=7.0 Hz), a peak of COOH was not observed;

MS (ESI) m/z 428 (M+H)⁺, 426 (M–H)⁻.

Example 7

4-[(1S)-1-({5-chloro-2-[(2,3-difluorophenoxy)methyl]benzoyl}amino)ethyl]benzoic Acid

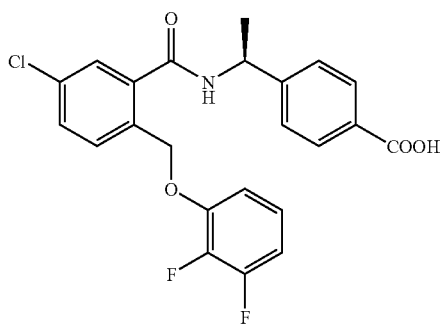

STEP 1. Methyl 5-chloro-2-[(2,3-difluorophenoxy)methyl]benzoate

The title compound was prepared according to the procedure described in step 1 of Example 1 from methyl 2-(bromoethyl)-5-chlorobenzoate and 2,3-difluorophenol:

¹H-NMR (CDCl₃) δ 8.03 (1H, d, J=2.3 Hz), 7.76 (1H, d, J=8.5 Hz), 7.55 (1H, dd, J=8.5, 2.3 Hz), 7.02-6.92 (1H, m), 6.84-6.75 (2H, m), 5.53 (2H, s), 3.93 (3H, s).

STEP 2. 5-Chloro-2-[(2,3-difluorophenoxy)methyl]benzoic acid

The title compound was prepared according to the procedure described in step 2 of Example 1 from methyl 5-chloro-2-[(2,3-difluorophenoxy)methyl]benzoate (step 1):

¹H-NMR (DMSO-d₆) δ 7.92-7.91 (1H, m), 7.74-7.65 (2H, m), 7.19-7.10 (1H, m), 7.06-6.97 (2H, m), 5.53 (2H, s), a peak of COOH was not observed;

MS (ESI) m/z 297 (M–H)⁻.

STEP 3. Methyl 4-[(1S)-1-({5-chloro-2-[(2,3-difluorophenoxy)methyl]benzoyl}amino)ethyl]benzoate The title compound was prepared according to the procedure described in step 6 of Example 1 from 5-chloro-2-[(2,3-difluorophenoxy)methyl]benzoic acid (step 2) and methyl 4-[(1S)-1-aminoethyl]benzoate hydrochloride (step 5 of Example 1):

¹H-NMR (CDCl₃) δ 7.94-7.91 (2H, m), 7.59 (1H, br.s), 7.45 (2H, br.s), 7.39-7.35 (2H, m), 7.00-6.64 (4H, m), 5.35-5.24 (1H, m), 5.18-5.08 (2H, m), 3.91 (3H, s), 1.53 (3H, d, J=7.1 Hz);

MS (ESI) m/z 460 (M+H)⁺.

STEP 4. 4-[(1S)-1-({5-Chloro-2-[(2,3-difluorophenoxy)methyl]benzoyl}amino)ethyl]benzoic acid The title compound was prepared according to the procedure described in step 7 of Example 1 from methyl 4-[(1S)-1-({5-chloro-2-[(2,3-difluorophenoxy)methyl]benzoyl}amino)ethyl]benzoate (step 3):

¹H-NMR (DMSO-d₆) δ 9.10-9.07 (1H, m), 7.85-7.82 (2H, m), 7.63 (3H, br.s), 7.47-7.44 (2H, m), 7.09-6.90 (3H, m), 5.30-5.05 (3H, m), 1.43 (3H, d, J=7.0 Hz), a peak of COOH was not observed;

MS (ESI) m/z 446 (M+H)⁺, 444 (M–H)⁻.

Example 8

4-[(1S)-1-({5-chloro-2-[(2,4-difluorophenoxy)methyl]benzoyl}amino)ethyl]benzoic Acid

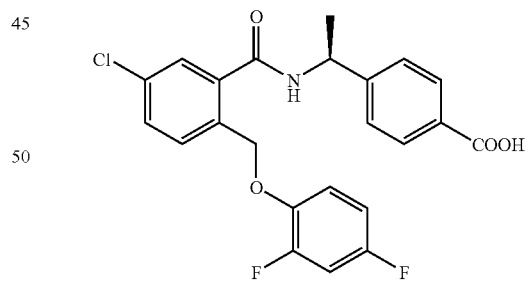

STEP 1. Methyl 5-chloro-2-[(2,4-difluorophenoxy)methyl]benzoate

The title compound was prepared according to the procedure described in step 1 of Example 1 from methyl 2-(bromoethyl)-5-chlorobenzoate and 2,4-difluorophenol:

¹H-NMR (CDCl₃) δ 8.02 (1H, d, J=2.2 Hz), 7.78-7.75 (1H, m), 7.57-7.53 (1H, m), 7.01-6.73 (3H, m), 5.48 (2H, s), 3.92 (3H, s).

STEP 2.
5-Chloro-2-[(2,4-difluorophenoxy)methyl]benzoic acid

The title compound was prepared according to the procedure described in step 2 of Example 1 from methyl 5-chloro-2-[(2,4-difluorophenoxy)methyl]benzoate (step 1):

$^1$H-NMR (DMSO-d$_6$) δ 7.91-7.90 (1H, m), 7.74-7.65 (2H, m), 7.36-7.27 (1H, m), 7.24-7.15 (1H, m), 7.06-6.97 (1H, m), 5.47 (2H, s), a peak of COOH was not observed;

MS (ESI) m/z 297 (M−H)$^−$.

STEP 3. Methyl 4-[(1S)-1-({5-chloro-2-[(2,4-difluorophenoxy)methyl]benzoyl}amino)ethyl]benzoate The title compound was prepared according to the procedure described in step 6 of Example 1 from 5-chloro-2-[(2,4-difluorophenoxy)methyl]benzoic acid (step 2) and methyl 4-[(1S)-1-aminoethyl]benzoate hydrochloride (step 5 of Example 1):

$^1$H-NMR (CDCl$_3$) δ 7.94-7.91 (2H, m), 7.61 (1H, br.s), 7.42 (2H, br.s), 7.39-7.36 (2H, m), 6.93-6.73 (4H, m), 5.35-5.25 (1H, m), 5.07 (2H, s), 3.91 (3H, s), 1.53 (3H, d, J=6.9 Hz);

MS (ESI) m/z 460 (M+H)$^+$.

STEP 4. 4-[(1S)-1-({5-Chloro-2-[(2,4-difluorophenoxy)methyl]benzoyl}amino)ethyl]benzoic acid The title compound was prepared according to the procedure described in step 7 of Example 1 from methyl 4-[(1S)-1-({5-chloro-2-[(2,4-difluorophenoxy)methyl]benzoyl}amino)ethyl]benzoate (step 3):

$^1$H-NMR (DMSO-d$_6$) δ 9.10-9.07 (1H, m), 7.85-7.82 (2H, m), 7.59 (3H, br.s), 7.48-7.45 (2H, m), 7.30-7.21 (1H, m), 7.12-7.03 (1H, m), 6.98-6.90 (1H, m), 5.26-5.05 (3H, m), 1.43 (3H, d, J=7.0 Hz), a peak of COOH was not observed;

MS (ESI) m/z 446 (M+H)$^+$, 444 (M−H)$^−$.

Example 9

4-[(1S)-1-({5-chloro-2-[(2,5-difluorophenoxy)methyl]benzoyl}amino)ethyl]benzoic Acid

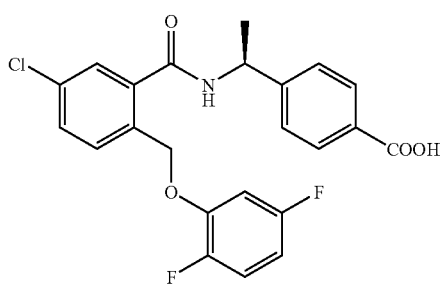

STEP 1. Methyl 5-chloro-2-[(2,5-difluorophenoxy)methyl]benzoate

The title compound was prepared according to the procedure described in step 1 of Example 1 from methyl 2-(bromoethyl)-5-chlorobenzoate and 2,5-difluorophenol:

$^1$H-NMR (CDCl$_3$) δ 8.03 (1H, d, J=2.2 Hz), 7.74 (1H, d, J=8.4 Hz), 7.55 (1H, dd, J=8.4, 2.2 Hz), 7.10-7.01 (1H, m), 6.80-6.73 (1H, m), 6.65-6.57 (1H, m), 5.50 (2H, s), 3.93 (3H, s).

STEP 2.
5-Chloro-2-[(2,5-difluorophenoxy)methyl]benzoic acid

The title compound was prepared according to the procedure described in step 2 of Example 1 from methyl 5-chloro-2-[(2,5-difluorophenoxy)methyl]benzoate (step 1):

$^1$H-NMR (DMSO-d$_6$) δ 7.89-7.88 (1H, m), 7.71-7.62 (2H, m), 7.31-7.23 (1H, m), 7.15-7.09 (1H, m), 6.82-6.75 (1H, m), 5.48 (2H, s), a peak of COOH was not observed.

STEP 3. Methyl 4-[(1S)-1-({5-chloro-2-[(2,5-difluorophenoxy)methyl]benzoyl}amino)ethyl]benzoate The title compound was prepared according to the procedure described in step 6 of Example 1 from 5-chloro-2-[(2,5-difluorophenoxy)methyl]benzoic acid (step 2) and methyl 4-[(1S)-1-aminoethyl]benzoate hydrochloride (step 5 of Example 1):

$^1$H-NMR (CDCl$_3$) δ 7.95-7.92 (2H, m), 7.59 (1H, br.s), 7.48-7.42 (2H, m), 7.39-7.36 (2H, m), 7.05-6.96 (1H, m), 6.72-6.58 (3H, m), 5.36-5.25 (1H, m), 5.14-5.04 (2H, m), 3.91 (3H, s), 1.53 (3H, d, J=7.1 Hz);

MS (ESI) m/z 460 (M+H)$^+$.

STEP 4. 4-[(1S)-1-({5-Chloro-2-[(2,5-difluorophenoxy)methyl]benzoyl}amino)ethyl]benzoic acid The title compound was prepared according to the procedure described in step 7 of Example 1 from methyl 4-[(1S)-1-({5-chloro-2-[(2,5-difluorophenoxy)methyl]benzoyl}amino)ethyl]benzoate (step 3):

$^1$H-NMR (DMSO-d$_6$) δ 9.11-9.09 (1H, m), 7.84-7.81 (2H, m), 7.60 (3H, br.s), 7.48-7.45 (2H, m), 7.30-7.20 (1H, m), 7.09-7.01 (1H, m), 6.80-6.72 (1H, m), 5.23 (2H, s), 5.15-5.05 (1H, m), 1.43 (3H, d, J=7.0 Hz), a peak of COOH was not observed;

MS (ESI) m/z 446 (M+H)$^+$, 444 (M−H)$^−$.

Example 10

4-[(1S)-1-({5-chloro-2-[(2,6-difluorophenoxy)methyl]benzoyl}amino)ethyl]benzoic Acid

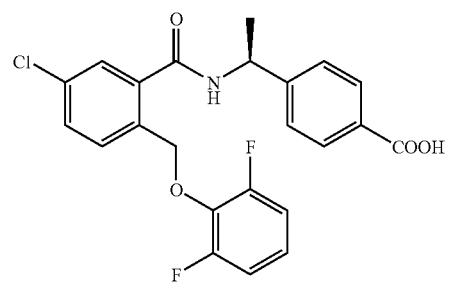

STEP 1. Methyl 5-chloro-2-[(2,6-difluorophenoxy)methyl]benzoate

The title compound was prepared according to the procedure described in step 1 of Example 1 from methyl 2-(bromoethyl)-5-chlorobenzoate and 2,6-difluorophenol:
$^1$H-NMR (CDCl$_3$) δ 7.99 (1H, d, J=2.3 Hz), 7.84 (1H, d, J=8.4 Hz), 7.56 (1H, dd, J=8.4, 2.3 Hz), 7.03-6.84 (3H, m), 5.55 (2H, s), 3.90 (3H, s).

STEP 2. 5-Chloro-2-[(2,6-difluorophenoxy)methyl]benzoic acid

The title compound was prepared according to the procedure described in step 2 of Example 1 from methyl 5-chloro-2-[(2,6-difluorophenoxy)methyl]benzoate (step 1):
$^1$H-NMR (DMSO-d$_6$) δ 7.88-7.87 (1H, m), 7.77-7.69 (2H, m), 7.16-7.12 (3H, m), 5.53 (2H, s), a peak of COOH was not observed.

STEP 3. Methyl 4-[(1S)-1-({5-chloro-2-[(2,6-difluorophenoxy)methyl]benzoyl}amino)ethyl]benzoate The title compound was prepared according to the procedure described in step 6 of Example 1 from 5-chloro-2-[(2,6-difluorophenoxy)methyl]benzoic acid (step 2) and methyl 4-[(1S)-1-aminoethyl]benzoate hydrochloride (step 5 of Example 1):
$^1$H-NMR (CDCl$_3$) δ 8.03-8.00 (2H, m), 7.65-7.64 (1H, m), 7.49-7.46 (2H, m), 7.34-7.21 (4H, m), 7.03-6.85 (2H, m), 5.42-5.18 (3H, m), 3.91 (3H, s), 1.61 (3H, d, J=6.9 Hz);
MS (ESI) m/z 460 (M+H)$^+$.

STEP 4. 4-[(1S)-1-({5-Chloro-2-[(2,6-difluorophenoxy)methyl]benzoyl}amino)ethyl]benzoic acid The title compound was prepared according to the procedure described in step 7 of Example 1 from methyl 4-[(1S)-1-({5-chloro-2-[(2,6-difluorophenoxy)methyl]benzoyl}amino)ethyl]benzoate (step 3):
$^1$H-NMR (DMSO-d$_6$) δ 9.06-9.04 (1H, m), 7.89-7.86 (2H, m), 7.69-7.59 (3H, m), 7.49-7.46 (2H, m), 7.13-7.09 (3H, m), 5.33-5.23 (2H, m), 5.15-5.05 (1H, m), 1.43 (3H, d, J=6.8 Hz), a peak of COOH was not observed;
MS (ESI) m/z 446 (M+H)$^+$, 444 (M−H)$^−$.

Example 11

4-[(1S)-1-({5-chloro-2-[(3,4-difluorophenoxy)methyl]benzoyl}amino)ethyl]benzoic Acid

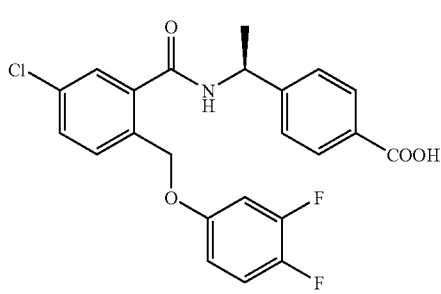

STEP 1. Methyl 5-chloro-2-[(3,4-difluorophenoxy)methyl]benzoate

The title compound was prepared according to the procedure described in step 1 of Example 1 from methyl 2-(bromoethyl)-5-chlorobenzoate and 3,4-difluorophenol:
$^1$H-NMR (CDCl$_3$) δ 8.02 (1H, d, J=2.3 Hz), 7.66 (1H, d, J=8.4 Hz), 7.53 (1H, dd, J=8.4, 2.3 Hz), 7.13-7.02 (1H, m), 6.85-6.77 (1H, m), 6.71-6.65 (1H, m), 5.41 (2H, s), 3.92 (3H, s).

STEP 2. 5-Chloro-2-[(3,4-difluorophenoxy)methyl]benzoic acid

The title compound was prepared according to the procedure described in step 2 of Example 1 from methyl 5-chloro-2-[(3,4-difluorophenoxy)methyl]benzoate (step 1):
$^1$H-NMR (DMSO-d$_6$) δ 7.88-7.87 (1H, m), 7.69-7.61 (2H, m), 7.40-7.30 (1H, m), 7.16-7.08 (1H, m), 6.82-6.77 (1H, m), 5.59 (2H, s), a peak of COOH was not observed.

STEP 3. Methyl 4-[(1S)-1-({5-chloro-2-[(3,4-difluorophenoxy)methyl]benzoyl}amino)ethyl]benzoate The title compound was prepared according to the procedure described in step 6 of Example 1 from 5-chloro-2-[(3,4-difluorophenoxy)methyl] benzoic acid (step 2) and methyl 4-[(1S)-1-aminoethyl]benzoate hydrochloride (step 5 of Example 1):
$^1$H-NMR (CDCl$_3$) δ 7.93-7.90 (2H, m), 7.59 (1H, br.s), 7.45-7.44 (2H, m), 7.36-7.32 (2H, m), 7.09-6.99 (1H, m), 6.68-6.60 (1H, m), 6.58-6.50 (2H, m), 5.34-5.24 (1H, m), 5.04-4.95 (2H, m), 3.92 (3H, s), 1.52 (3H, d, J=6.9 Hz);
MS (ESI) m/z 460 (M+H)$^+$.

STEP 4. 4-[(1S)-1-({5-Chloro-2-[(3,4-difluorophenoxy)methyl]benzoyl}amino)ethyl]benzoic acid The title compound was prepared according to the procedure described in step 7 of Example 1 from methyl 4-[(1S)-1-({5-chloro-2-[(3,4-difluorophenoxy)methyl] benzoyl}amino) ethyl]benzoate (step 3):
$^1$H-NMR (DMSO-d$_6$) δ 9.08-9.05 (1H, m), 7.87-7.82 (2H, m), 7.57 (3H, br.s), 7.48-7.45 (2H, m), 7.35-7.23 (1H, m), 6.98-6.90 (1H, m), 6.68-6.64 (1H, m), 5.16-5.06 (3H, m), 1.43 (3H, d, J=6.8 Hz), a peak of COOH was not observed;
MS (ESI) m/z 446 (M+H)$^+$, 444 (M−H)$^−$.

Example 12

4-[(1S)-1-({5-chloro-2-[(3,5-difluorophenoxy)methyl]benzoyl}amino)ethyl]benzoic Acid

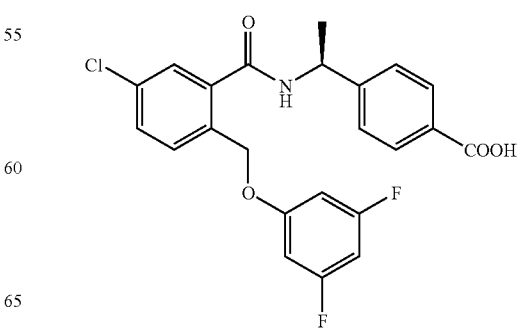

STEP 1. Methyl 5-chloro-2-[(3,5-difluorophenoxy)methyl]benzoate

The title compound was prepared according to the procedure described in step 1 of Example 1 from methyl 2-(bromoethyl)-5-chlorobenzoate and 3,5-difluorophenol:
$^1$H-NMR (CDCl$_3$) δ 8.04-8.03 (1H, m), 7.66-7.63 (1H, m), 7.56-7.52 (1H, m), 6.59-6.40 (3H, m), 5.43 (2H, s), 3.92 (3H, s).

STEP 2. 5-Chloro-2-[(3,5-difluorophenoxy)methyl]benzoic acid

The title compound was prepared according to the procedure described in step 2 of Example 1 from methyl 5-chloro-2-[(3,5-difluorophenoxy)methyl]benzoate (step 1):
$^1$H-NMR (DMSO-d$_6$) δ 7.88 (1H, d, J=2.2 Hz), 7.69-7.60 (2H, m), 6.84-6.74 (3H, m), 5.42 (2H, s), a peak of COOH was not observed.

STEP 3. Methyl 4-[(1S)-1-({5-chloro-2-[(3,5-difluorophenoxy)methyl]benzoyl}amino)ethyl]benzoate The title compound was prepared according to the procedure described in step 6 of Example 1 from 5-chloro-2-[(3,5-difluorophenoxy)methyl]benzoic acid (step 2) and methyl 4-[(1S)-1-aminoethyl]benzoate hydrochloride (step 5 of Example 1):
$^1$H-NMR (CDCl$_3$) δ 7.96-7.93 (2H, m), 7.57 (1H, br.s), 7.45-7.44 (2H, m), 7.37-7.34 (2H, m), 6.49-6.33 (4H, m), 5.35-5.24 (1H, m), 5.04 (2H, s), 3.92 (3H, s), 1.53 (3H, d, J=6.9 Hz);
MS (ESI) m/z 460 (M+H)$^+$.

STEP 4. 4-[(1S)-1-({5-Chloro-2-[(3,5-difluorophenoxy)methyl]benzoyl}amino)ethyl]benzoic acid The title compound was prepared according to the procedure described in step 7 of Example 1 from methyl 4-[(1S)-1-({5-chloro-2-[(3,5-difluorophenoxy)methyl]benzoyl}amino)ethyl]benzoate (step 3):
$^1$H-NMR (DMSO-d$_6$) δ 9.09-9.06 (1H, m), 7.86-7.83 (2H, m), 7.58 (3H, br.s), 7.49-7.46 (2H, m), 6.80-6.71 (1H, m), 6.64-6.57 (2H, m), 5.22-5.05 (3H, m), 1.43 (3H, d, J=7.0 Hz), a peak of COOH was not observed;
MS (ESI) m/z 446 (M+H)$^+$, 444 (M−H)$^−$.

Example 13

4-[(1S)-1-({5-chloro-2-[(4-methylphenoxy)methyl]benzoyl}amino)ethyl]benzoic Acid

STEP 1. Methyl 5-chloro-2-[(4-methylphenoxy)methyl]benzoate

The title compound was prepared according to the procedure described in step 1 of Example 1 from methyl 2-(bromoethyl)-5-chlorobenzoate and 4-methylphenol:
$^1$H-NMR (CDCl$_3$) δ 8.00 (1H, d, J=2.3 Hz), 7.71 (1H, d, J=8.4 Hz), 7.51 (1H, dd, J=8.4, 2.3 Hz), 7.10-7.07 (2H, m), 6.89-6.85 (2H, m), 5.43 (2H, s), 3.91 (3H, s), 2.29 (3H, s).

STEP 2. 5-Chloro-2-[(4-methylphenoxy)methyl]benzoic acid

The title compound was prepared according to the procedure described in step 2 of Example 1 from methyl 5-chloro-2-[(4-methylphenoxy)methyl]benzoate (step 1):
$^1$H-NMR (DMSO-d$_6$) δ 7.85 (1H, m), 7.65-7.59 (2H, m), 7.09-7.06 (2H, m), 6.85-6.82 (2H, m), 5.37 (2H, s), 2.21 (3H, s), a peak of COOH was not observed.

STEP 3. Methyl 4-[(1S)-1-({5-chloro-2-[(4-methylphenoxy)methyl]benzoyl}amino)ethyl]benzoate The title compound was prepared according to the procedure described in step 6 of Example 1 from 5-chloro-2-[(4-methylphenoxy)methyl]benzoic acid (step 2) and methyl 4-[(1S)-1-aminoethyl]benzoate hydrochloride (step 5 of Example 1):
$^1$H-NMR (CDCl$_3$) δ 7.89-7.86 (2H, m), 7.68 (1H, br.s), 7.45-7.39 (2H, m), 7.29-7.26 (2H, m), 7.10-7.07 (2H, m), 7.01-6.99 (1H, m), 6.78-6.75 (2H, m), 5.33-5.22 (1H, m), 5.02-4.93 (2H, m), 3.91 (3H, s), 2.31 (3H, s), 1.42 (3H, d, J=6.9 Hz);
MS (ESI) m/z 438 (M+H)$^+$, 436 (M−H)$^−$.

STEP 4. 4-[(1S)-1-({5-Chloro-2-[(4-methylphenoxy)methyl]benzoyl}amino)ethyl]benzoic acid The title compound was prepared according to the procedure described in step 7 of Example 1 from methyl 4-[(1S)-1-({5-chloro-2-[(4-methylphenoxy)methyl]benzoyl}amino)ethyl]benzoate (step 3):
$^1$H-NMR (DMSO-d$_6$) δ 9.07-9.04 (1H, m), 7.86-7.83 (2H, m), 7.60-7.53 (3H, m), 7.49-7.46 (2H, m), 7.05-7.02 (2H, m), 6.74-6.71 (2H, m), 5.15-5.03 (3H, m), 2.22 (3H, s), 1.43 (3H, d, J=7.3 Hz), a peak of COOH was not observed;
MS (ESI) m/z 424 (M+H)$^+$, 422 (M−H)$^−$.

Example 14

4-{(1S)-1-[(5-chloro-2-{[(5-fluoropyridin-3-yl)oxy]methyl}benzoyl)amino]ethyl}benzoic Acid

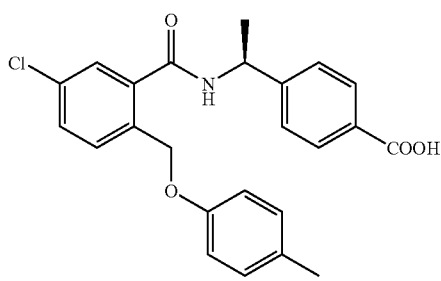

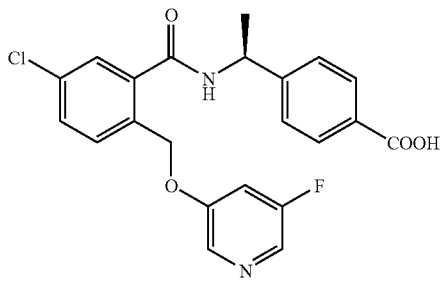

STEP 1. Methyl 5-chloro-2-{[(5-fluoropyridin-3-yl) oxy]methyl}benzoate

To a solution of 3-fluoro-5-hydroxypyridine (34 mg, 0.30 mmol) in dimethylformamide (3 mL) was added sodium hydride (60% dispersion in mineral oil, 12 mg, 0.30 mmol) at 0° C. and the mixture was stirred at room temperature for 15 minutes. To the mixture was added methyl 2-(bromomethyl)-5-chlorobenzoate (100 mg, 0.4 mmol) in dimethylformamide and the mixture was stirred at room temperature overnight. The mixture was quenched with water and extracted with ethyl acetate. The organic layer was washed with brine, dried over sodium sulfate and evaporated. The residue was purified by flash column chromatography on silica gel to afford 47 mg (53%) of the title compound:

$^1$H-NMR (CDCl$_3$) δ 8.25 (1H, d, J=1.5 Hz), 8.14 (1H, d, J=2.2 Hz), 8.05 (1H, d, J=2.2 Hz), 7.66 (1H, d, J=8.4 Hz), 7.57 (1H, dd, J=8.4, 2.2 Hz), 7.10-7.00 (1H, m), 5.51 (2H, s), 3.93 (3H, s).

STEP 2. 5-Chloro-2-{[(5-fluoropyridin-3-yl)oxy] methyl}benzoic acid

The title compound was prepared according to the procedure described in step 2 of Example 1 from methyl 5-chloro-2-{[(5-fluoropyridin-3-yl)oxy]methyl}benzoate (step 1). The title compound was used in the next step without further purification:

MS (ESI) m/z 280 (M−H)$^−$.

STEP 3. Methyl 4-((1S)-1-[(5-chloro-2-{[(5-fluoropyridin-3-yl)oxy]methylbenzoyl)amino] ethyl}benzoate The title compound was prepared according to the procedure described in step 6 of Example 1 from 5-chloro-2-{[(5-fluoropyridin-3-yl)oxy]methyl}benzoic acid (step 2) and methyl 4-[(1S)-1-aminoethyl]benzoate hydrochloride (step 5 of Example 1):

$^1$H-NMR (CDCl$_3$) δ 8.18-8.10 (2H, m), 7.95 (2H, d, J=8.3 Hz), 7.60-7.43 (3H, m), 7.38 (2H, d, J=8.3 Hz), 6.89 (1H, dt, J=10.0, 2.4 Hz), 6.49-6.42 (1H, m), 5.37-5.22 (1H, m), 5.16 (2H, s), 3.92 (3H, s), 1.55 (3H, d, J=7.0 Hz);

MS (ESI) m/z 443 (M+H)$^+$.

STEP 4. 4-{(1S)-1-[(5-Chloro-2-{[(5-fluoropyridin-3-yl)oxy]methyl}benzoyl)amino]ethyl}benzoic acid The title compound was prepared according to the procedure described in step 7 of Example 1 from methyl 4-{(1S)-1-[(5-chloro-2-{[(5-fluoropyridin-3-yl)oxy] methyl}benzoyl)amino]ethyl}benzoate (step 3):

$^1$H-NMR (DMSO-d$_6$) δ 9.10 (1H, d, J=8.1 Hz), 8.23-8.09 (2H, m), 7.84 (2H, d, J=8.2 Hz), 7.60-7.50 (3H, m), 7.47 (2H, d, J=8.2 Hz), 7.38-7.28 (1H, m), 5.25 (2H, s), 5.10 (1H, dq, J=8.1, 6.9 Hz), 1.43 (3H, d, J=6.9 Hz);

MS (ESI) m/z 429 (M+H)$^+$, 427 (M−H)$^−$.

Example 15

4-{(1S)-1-[(5-chloro-2-{[(5-chloropyridin-3-yl)oxy] methyl}benzoyl)amino]ethyl}benzoic Acid

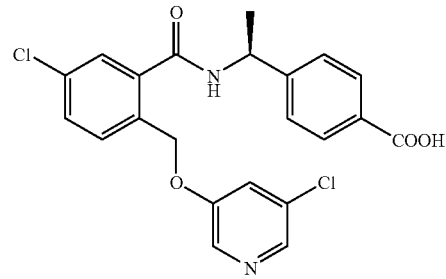

STEP 1. Methyl 5-chloro-2-{[(5-chloropyridin-3-yl) oxy]methyl}benzoate

The title compound was prepared according to the procedure described in step 1 of Example 1 from methyl 2-(bromomethyl)-5-chlorobenzoate and 3-chloro-5-hydroxypyridine:

$^1$H-NMR (CDCl$_3$) δ 8.29 (1H, d, J=2.8 Hz), 8.22 (1H, d, J=2.0 Hz), 8.05 (1H, d, J=2.2 Hz), 7.66 (1H, d, J=8.4 Hz), 7.56 (1H, dd, J=8.4, 2.2 Hz), 7.35-7.25 (1H, m), 5.50 (2H, s), 3.92 (3H, s).

STEP 2. 5-Chloro-2-{[(5-chloropyridin-3-yl)oxy] methyl}benzoic acid

The title compound was prepared according to the procedure described in step 2 of Example 1 from methyl 5-chloro-2-([(5-chloropyridin-3-yl)oxy]methylbenzoate (step 1): MS (ESI) m/z 296 (M−H)$^−$.

STEP 3. Methyl 4-{(1S)-1-[(5-chloro-2-{[(5-chloropyridin-3-yl)oxy]methyl}benzoyl)amino] ethyl}benzoate The title compound was prepared according to the procedure described in step 6 of Example 1 from 5-chloro-2-{[(5-chloropyridin-3-yl)oxy]methyl}benzoic acid (step 2) and methyl 4-[(1S)-1-aminoethyl]benzoate hydrochloride (step 5 of Example 1):

$^1$H-NMR (CDCl$_3$) δ 8.23-8.15 (2H, m), 7.95 (2H, d, J=8.3 Hz), 7.57-7.54 (1H, m), 7.48 (2H, s), 7.38 (2H, d, J=8.3 Hz), 7.15 (1H, t, J=2.2 Hz), 6.45-6.35 (1H, m), 5.35-5.22 (1H, m), 5.15 (2H, s), 3.92 (3H, s), 1.56 (3H, d, J=7.0 Hz);

MS (ESI) m/z 459 (M+H)$^+$.

STEP 4. 4-{(1S)-1-[(5-Chloro-2-{[(5-chloropyridin-3-yl)oxy]methyl}benzoyl)amino]ethyl}benzoic acid The title compound was prepared according to the procedure described in step 7 of Example 1 from 4-{(1S)-1-[(5-chloro-2-{[(5-chloropyridin-3-yl)oxy]methyl}benzoyl) amino]ethyl}benzoate (step 3):

$^1$H-NMR (DMSO-d$_6$) δ 9.09 (1H, d, J=8.6 Hz), 8.23-8.15 (2H, m), 7.84 (2H, d, J=8.2 Hz), 7.60 (3H, br.s), 7.50-7.40 (3H, m), 5.34-5.20 (2H, m), 5.19-5.00 (1H, m), 1.43 (3H, d, J=6.9 Hz);

MS (ESI) m/z 445 (M+H)$^+$, 443 (M−H)$^−$.

Example 16

4-[(1S)-1-({5-chloro-2-[(cyclopentyloxy)methyl]benzoyl}amino)ethyl]benzoic Acid

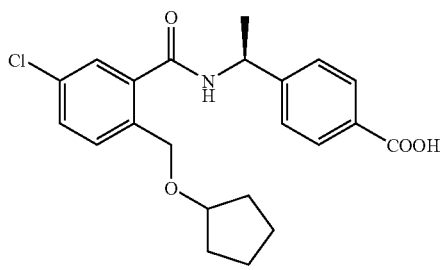

STEP 1. 5-Chloro-2-[(cyclopentyloxy)methyl]benzoic acid

A mixture of methyl 2-(bromomethyl)-5-chlorobenzoate (200 mg, 0.80 mmol), cyclopentanol (379 mg 4.4 mmol), and potassium tert-butoxide (448 mg, 4.0 mmol) in tetrahydrofuran (8 mL) was stirred at room temperature for 3 hours. The mixture was acidified with 2 N hydrochloric acid and the acidic aqueous mixture was extracted with ethyl acetate. The organic layer was washed with brine, dried over sodium sulfate and evaporated. The residue was purified by flash column chromatography on silica gel eluting with hexane/ethyl acetate (1/1) to afford 100 mg (49%) of the title compound:

$^1$H-NMR (CDCl$_3$) δ 8.05 (1H, d, J=2.2 Hz), 7.58 (1H, d, J=8.4 Hz), 7.52 (1H, dd, J=8.4, 2.2 Hz), 4.78 (2H, s), 4.15-4.05 (1H, m), 1.90-1.50 (8H, m);
MS (ESI) m/z 253 (M−H)$^−$.

STEP 2. Methyl 4-[(1S)-1-({5-chloro-2-[(cyclopentyloxy)methyl]benzoyl}amino)ethyl]benzoate The title compound was prepared according to the procedure described in step 6 of Example 1 from 5-chloro-2-[(cyclopentyloxy)methyl]benzoic acid (step 1) and methyl 4-[(1S)-1-aminoethyl]benzoate hydrochloride (step 5 of Example 1):

$^1$H-NMR (DMSO-d$_6$) δ 8.17-8.07 (1H, m), 8.03 (2H, d, J=8.4 Hz), 7.80 (1H, d, J=2.1 Hz), 7.47 (2H, d, J=8.4 Hz), 7.38 (1H, dd, J=8.1, 2.1 Hz), 7.25 (1H, d, J=8.1 Hz), 5.45-5.30 (1H, m), 4.50 (1H, d, J=11.7 Hz), 4.44 (1H, d, J=11.7 Hz), 3.98-3.87 (4H, m), 1.80-1.40 (11H, m);
MS (ESI) m/z 416 (M+H)$^+$, 414 (M−H)$^−$.

STEP 3. 4-[(1S)-1-({5-Chloro-2-[(cyclopentyloxy)methyl]benzoyl}amino)ethyl]benzoic acid The title compound was prepared according to the procedure described in step 7 of Example 1 from methyl 4-[(1S)-1-({5-chloro-2-[(cyclopentyloxy)methyl]benzoyl}amino)ethyl]benzoate (step 2):

$^1$H-NMR (DMSO-d$_6$) δ 8.97 (1H, d, J=7.7 Hz), 7.93 (2H, d, J=7.9 Hz), 7.60-7.40 (5H, m), 5.22-5.04 (1H, m), 4.42 (2H, s), 3.90-3.80 (1H, br), 1.70-1.35 (11H, m);
MS (ESI) m/z 402 (M+H)$^+$, 400 (M−H)$^−$.

Example 17

4-((1S)-1-{[5-chloro-2-(isobutoxymethyl)benzoyl]amino}ethyl)benzoic Acid

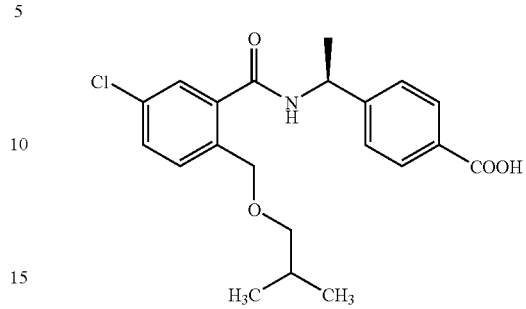

STEP 1. 5-Chloro-2-(isobutoxymethyl)benzoic acid

The title compound was prepared according to the procedure described in step 1 of Example 16 from methyl 2-(bromomethyl)-5-chlorobenzoate and 2-methylpropan-1-ol:

$^1$H-NMR (CDCl$_3$) δ 8.05 (1H, d, J=2.4 Hz), 7.61 (1H, d, J=8.4 Hz), 7.53 (1H, dd, J=8.4, 2.4 Hz), 4.82 (2H, s), 3.36 (2H, d, J=6.4 Hz), 2.05-1.88 (1H, m), 0.96 (6H, d, J=6.6 Hz);
MS (ESI) m/z 241 (M−H)$^−$.

STEP 2. Methyl 4-((1S)-1-{[5-chloro-2-(isobutoxymethyl)benzoyl]amino}ethyl)benzoate The title compound was prepared according to the procedure described in step 6 of Example 1 from 5-chloro-2-(isobutoxymethyl)benzoic acid (step 1) and methyl 4-[(1S)-1-aminoethyl]benzoate hydrochloride (step 5 of Example 1):
MS (ESI) m/z 404 (M+H)$^+$, 402 (M−H)$^−$.

STEP 3. 4-((1S)-1-{[5-Chloro-2-(isobutoxymethyl)benzoyl]amino}ethyl)benzoic acid The title compound was prepared according to the procedure described in step 7 of Example 1 from methyl 4-((1S)-1-{[5-chloro-2-(isobutoxymethyl)benzoyl]amino}ethyl)benzoate (step 2):

$^1$H-NMR (DMSO-d$_6$) δ 8.97 (1H, d, J=8.1 Hz), 7.92 (2H, d, J=7.9 Hz), 7.55-7.45 (5H, m), 5.12 (1H, dq, J=8.1, 7.0 Hz), 4.49 (1H, d, J=13.0 Hz), 4.44 (1H, d, J=13.0 Hz), 3.09 (2H, d, J=6.2 Hz), 1.80-1.65 (1H, m), 1.44 (3H, d, J=7.0 Hz) 0.82 (6H, d, J=6.8 Hz);
MS (ESI) m/z 390 (M+H)$^+$, 388 (M−H)$^−$.

Example 18

4-{(1S)-1-[({5-chloro-2-[(4-chlorophenoxy)methyl]pyridin-3-yl}carbonyl)amino]ethyl}benzoic Acid

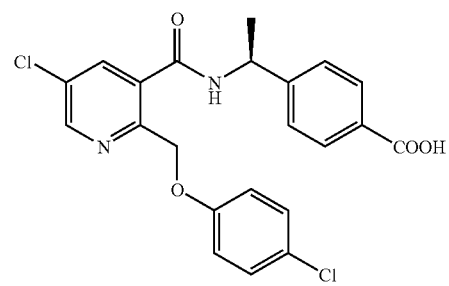

STEP 1. 3-Chlorofuro[3,4-b]pyridin-5 (7H)-one

A mixture of crude methyl 5-chloro-2-methylnicotinate 1-oxide (*Organic letters*, 2001, 3, 209, 2.29 mmol) and trifluoroacetic acid (453 μL, 3.21 mmol) in dichloromethane (20 mL) was stirred at room temperature for 2 days and heated at 45° C. for 1 hour. The mixture was partitioned between sat. aqueous sodium hydrogen carbonate (50 mL) and ethyl acetate (50 mL). The organic layer was washed with brine (50 mL), dried (sodium sulfate), and evaporated. The residue was purified by flash column chromatography on silica gel eluting with hexane/ethyl acetate (1/1) to afford 225 mg of the title compound.

$^1$H-NMR (CDCl$_3$) δ 8.55 (1H, d, J=2.0 Hz), 8.19 (1H, d, J=2.0 Hz), 5.34 (2H, s).

STEP 2. 5-Chloro-2-[(4-chlorophenoxy)methyl]nicotinic acid

A mixture of 3-chlorofuro[3,4-b]pyridin-5(7M-one (step 1, 110 mg, 0.65 mmol) and 4-choloro phenol (416 mg, 3.24 mmol) was heated to 130° C. under N$_2$, then sodium methoxide (28% methanol solution, 250 mg, 1.30 mmol) was added dropwise to the mixture at 130° C. The mixture was heated at the same temperature for 4 hours. After cooling, to the mixture was added 10% aqueous citric acid and the mixture was extracted with ethyl acetate. The extracts were dried over sodium sulfate and evaporated. The residue was purified by flash column chromatography on silica gel to afford 113 mg of the title compound:

MS (ESI) m/z 298 (M+H)$^+$, 296 (M–H)$^-$.

STEP 3. Methyl 4-{(1S)-1-[({5-chloro-2-[(4-chlorophenoxy)methyl]pyridin-3-yl}carbonyl)amino]ethyl}benzoate The title compound was prepared according to the procedure described in step 6 of Example 1 from 5-chloro-2-[(4-chlorophenoxy)methyl]nicotinic acid (step 2) and methyl 4-[(1S)-1-aminoethyl]benzoate hydrochloride (step 5 of Example 1):

MS (ESI) m/z 459 (M+H)$^+$, 457 (M–H)$^-$.

STEP 4. 4-{(1S)-1-[({5-Chloro-2-[(4-chlorophenoxy)methyl]pyridin-3-yl}carbonyl)amino]ethyl}benzoic acid The title compound was prepared according to the procedure described in step 7 of Example 1 from methyl 4-{(1S)-1-[({5-chloro-2-[(4-chlorophenoxy)methyl]pyridin-3-yl}carbonyl)amino]ethyl}benzoate (step 3):

$^1$H-NMR (DMSO-d$_6$) δ 9.17 (1H, d, J=7.5 Hz), 8.72 (1H, s), 8.08 (1H, s), 7.85 (2H, d, J=7.9 Hz), 7.46 (2H, d, J=7.9 Hz), 7.26 (2H, d, J=7.5 Hz), 6.83 (2H, d, J=7.5 Hz), 5.23 (1H, d, J=11.9 Hz), 5.18 (1H, d, J=11.9 Hz), 5.13-5.15 (1H, m), 1.41 (3H, d, J=7.3 Hz);

MS (ESI) m/z 445 (M+H)$^+$, 443 (M–H)$^-$.

Example 19

4-((1S)-1-{[5-chloro-2-({3-[(methylamino)carbonyl]phenoxy}methyl)benzoyl]amino}ethyl)benzoic Acid

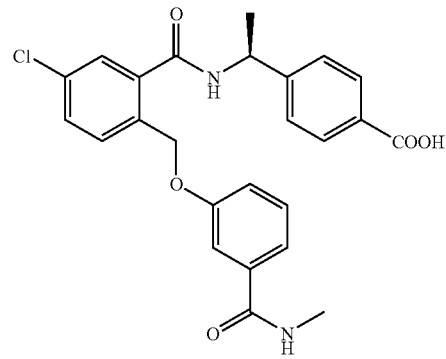

STEP 1. Methyl 5-chloro-2-({3-[(methylamino)carbonyl]phenoxy}methyl)benzoate The title compound was prepared according to the procedure described in step 1 of Example 1 from methyl 2-(bromoethyl)-5-chlorobenzoate and 3-hydroxy-N-methylbenzamide (WO 2003018566):

$^1$H-NMR (CDCl$_3$) δ 8.02 (1H, d, J=2.3 Hz), 7.68 (1H, d, J=8.4 Hz), 7.52 (1H, dd, J=8.4, 2.3 Hz), 7.43-7.29 (3H, m), 7.12-7.08 (1H, m), 5.49 (2H, s), 3.91 (3H, s), 3.01 (3H, d, J=4.9 Hz), a peak of NH was not observed;

MS (ESI) m/z 334 (M+H)$^+$.

STEP 2. 5-Chloro-2-({3-[(methylamino)carbonyl]phenoxy}methyl)benzoic acid

The title compound was prepared according to the procedure described in step 2 of Example 1 from methyl 5-chloro-2-({3-[(methylamino)carbonyl]phenoxy}methyl)benzoate (step 1):

$^1$H-NMR (DMSO-d$_6$) δ 8.43-8.41 (1H, m), 7.89 (1H, br.s), 7.70-7.63 (2H, m), 7.42-7.33 (3H, m), 7.12-7.09 (1H, m), 5.45 (2H, s), 2.75 (3H, d, J=4.5 Hz), a peak of COOH was not observed);

MS (ESI) m/z 320 (M+H)$^+$, 318 (M–H)$^-$.

STEP 3. Methyl 4-((1S)-1-{[5-chloro-2-({3-[(methylamino)carbonyl]phenoxy}methyl)benzoyl]amino}ethyl)benzoate The title compound was prepared according to the procedure described in step 6 of Example 1 from 5-chloro-2-({3-[(methylamino)carbonyl]phenoxy}methyl)benzoic acid (step 2) and methyl 4-[(1S)-1-aminoethyl]benzoate hydrochloride (step 3 of Example 1):

$^1$H-NMR (CDCl$_3$) δ 9.08 (1H, d, J=7.6 Hz), 8.40-8.39 (1H, m), 7.83 (2H, d, J=8.2 Hz), 7.61-7.54 (3H, m), 7.48 (2H, d, J=8.2 Hz), 7.42-7.38 (2H, m), 7.30 (1H, t, J=7.8 Hz), 6.97-6.94 (1H, m), 5.21-5.04 (3H, m), 3.81 (3H, s), 2.75 (3H, d, J=4.5 Hz), 1.41 (3H, d, J=7.1 Hz);

MS (ESI) m/z 481 (M+H)$^+$, 479 (M–H)$^-$.

STEP 4. 4-((1S)-1-{[5-Chloro-2-({3-[(methylamino)carbonyl]phenoxy}methyl)benzoyl]amino}ethyl)benzoic acid The title compound was prepared according to the procedure described in step 7 of Example 1 from methyl 4-((1S)-

1-{[5-chloro-2-({3-[(methylamino)carbonyl]phenoxy}methyl)benzoyl]amino}ethyl)benzoate (step 3):
$^1$H-NMR (DMSO-d$_6$) δ 8.97-8.94 (1H, m), 8.31-8.29 (1H, m), 7.76-7.73 (2H, m), 7.47-7.14 (8H, m), 6.89-6.84 (1H, m), 5.08-4.94 (3H, m), 2.65 (3H, d, J=4.3 Hz), 1.31 (3H, d, J=7.0 Hz), a peak of COOH was not observed;
MS (ESI) m/z 467 (M+H)$^+$, 465 (M−H)$^−$.

Example 20

4-{(1S)-1-[({5-chloro-2-[(3-chlorophenoxy)methyl]pyridin-3-yl}carbonyl)amino]ethyl}benzoic Acid

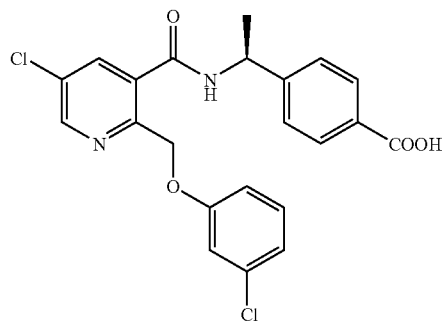

STEP 1.
5-Chloro-2-[(3-chlorophenoxy)methyl]nicotinic acid

The title compound was prepared according to the procedure described in step 2 of Example 18 from 3-chlorofuro[3,4-b]pyridin-5 (7H)-one (Organic letters, 2001, 3, 209.) and 3-choloro phenol:
MS (ESI) m/z 298 (M+H)$^+$, 296 (M−H)$^−$ STEP 2. Methyl 4-{(1S)-1-[({5-chloro-2-[(3-chlorophenoxy)methyl]pyridin-3-yl}carbonyl)amino]ethyl}benzoate The title compound was prepared according to the procedure described in step 3 of Example 1 from 5-chloro-2-[(3-chlorophenoxy)methyl]nicotinic acid (step 1) and methyl 4-[(1S)-1-aminoethyl]benzoate hydrochloride (step 5 of Example 1):
MS (ESI) m/z 459 (M+H)$^+$, 457 (M−H)$^−$ STEP 3. 4-{(1S)-1-[({5-Chloro-2-[(3-chlorophenoxy)methyl]pyridin-3-yl}carbonyl)amino]ethyl}benzoic acid The title compound was prepared according to the procedure described in step 3 of Example 1 from methyl 4-{(1S)-1-[({5-chloro-2-[(3-chlorophenoxy)methyl]pyridin-3-yl}carbonyl)amino]ethyl}benzoate (step 2):
$^1$H-NMR (DMSO-d$_6$) δ 9.16 (1H, d, J=8.9 Hz), 8.73 (1H, s), 8.09 (1H, s), 7.86 (2H, d, J=8.1 Hz), 7.45 (2H, d, J=8.1 Hz), 7.25 (1H, t, J=7.6 Hz), 6.99 (1H, d, J=7.6 Hz), 6.93 (1H, s), 6.85-6.75 (1H, m), 5.29-5.22 (2H, m), 5.20-5.00 (1H, m), 1.42 (3H, d, J=7.2 Hz);
MS (ESI) m/z 445 (M+H)$^+$, 443 (M−H)$^−$.

Example 21

4-{(1S)-1-[({2-[(4-chlorophenoxy)methyl]-5-fluoropyridin-3-yl}carbonyl)amino]ethyl}benzoic Acid

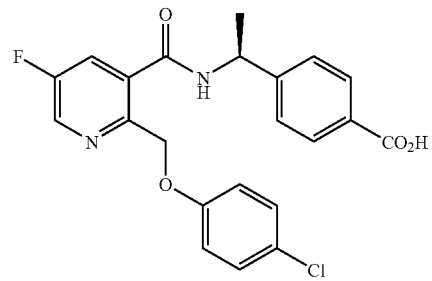

STEP 1. Methyl 2-chloro-5-fluoronicotinate

To a solution of 2-chloro-5-fluoronicotinic acid (5.2 g, 30 mmol) in methanol (20 ml) was added conc. sulfuric acid (0.5 ml) and the reaction mixture was stirred at reflux for 30 hours. The reaction mixture was cooled to 0° C. and 0.5 N sodium hydroxide solution was added to the mixture. The whole was extracted with diethylether. The organic phase was washed with brine, dried (sodium sulfate), and concentrated to afford 3.2 g (25%) of the title compound:
$^1$H-NMR (CDCl$_3$) δ 8.41 (1H, d, J=3.0 Hz), 7.93 (1H, dd, J=3.0, 7.6 Hz), 3.98 (3H, s).

STEP 2. Methyl 5-fluoro-2-methylnicotinate

A mixture of methyl 2-chloro-5-fluoronicotinate (step 1, 1.5 g, 7.91 mmol), tetrakis(triphenylphoshine)palladium (914 mg, 0.79 mmol), methyboronic acid (521 mg, 8.70 mmol) and potassium carbonate (3.28 g, 23.7 mmol) in 1,4-dioxane (20 ml) was heated at 110° C. for 20 h under nitrogen atmosphere. The reaction mixture was filtered through a pad of celite (Celite(trademark) (diatomaceous earth)) and the filtrate was concentrated. The residue was purified by flush column chromatography on silica gel eluting with hexane/ethyl acetate (20/1 to 4/1) to afford 936 mg (64%) of the title compound:
$^1$H-NMR (CDCl$_3$) δ 8.49 (1H, d, J=3.0 Hz), 7.93 (1H, dd, J=3.0, 8.7 Hz), 3.94 (3H, s), 2.81 (3H, s).

STEP 3. Methyl 5-fluoro-2-methylnicotinate 1-oxide

To a cooled (0° C.) solution of methyl 5-fluoro-2-methylnicotinate (step 2, 936 mg, 5.53 mmol) in dichloromethane (100 ml) was added 3-chlorobenzenecarboperoxoic acid (2.38 g, 13.8 mmol) and the reaction suspension was stirred overnight at room temperature. The reaction was quenched by the addition of sat. sodium thiosulfate solution and sat. sodium bicarbonate solution was added. The whole mixture was extracted with dichloromethane. The organic phase was dried over sodium sulfate and concentrated to afford 1.12 g (quant.) of title compound:
$^1$H-NMR (CDCl$_3$) δ 8.40-8.03 (1H, m), 7.52 (1H, dd, J=2.3, 7.7 Hz), 3.96 (3H, s), 2.73 (3H, s).

STEP 4. 3-Fluorofuro[3,4-b]pyridin-5 (7H)-one

The title compound was prepared according to the procedure described in step 1 of Example 18 from methyl 5-fluoro-2-methylnicotinate 1-oxide (step 3):

¹H-NMR (CDCl₃) δ 8.80-8.74 (1H, m), 7.89 (1H, dd, J=2.6, 6.6 Hz), 5.35 (2H, s).

STEP 5. 2-[(4-Chlorophenoxy)methyl]-5-fluoronicotinic acid

The title compound was prepared according to the procedure described in step 2 of Example 18 from 3-fluorofuro[3,4-b]pyridin-5(7H)-one (step 4) and 4-chlorophenol:
MS (ESI) m/z 282 (M+H)⁺, 280 (M−H)⁻.

STEP 6. Methyl 4-{(1S)-1-[({2-[(4-Chlorophenoxy)methyl]-5-fluoropyridin-3-yl}carbonyl)amino]ethyl}benzoate The title compound was prepared according to the procedure described in step 6 of Example 1 from 2-[(4-chlorophenoxy)methyl]-5-fluoronicotinic acid (step 5) and methyl 4-[(1S)-1-aminoethyl]benzoate hydrochloride (step 5 of Example 1):
¹H-NMR (CDCl₃) δ 8.54 (1H, d, J=3.0 Hz), 7.90 (2H, d, J=8.2 Hz), 7.80 (1H, dd, J=2.8, 8.2 Hz), 7.35-7.20 (5H, m), 6.83 (2H, d, J=9.1 Hz), 5.36-5.23 (1H, m), 5.17 (1H, d, J=10.1 Hz), 5.12 (1H, d, J=10.1 Hz), 3.93 (3H, s), 1.48 (3H, d, J=6.9 Hz).

STEP 7. 4-{(1S)-1-[({2-[(4-Chlorophenoxy)methyl]-5-fluoropyridin-3-yl}carbonyl)amino]ethyl}benzoic acid The title compound was prepared according to the procedure described in step 7 of Example 1 from methyl 4-{(1S)-1-[((2-[(4-chlorophenoxy)methyl]-5-fluoropyridin-3-yl)carbonyl)amino]ethyl}benzoate (step 6):
¹H-NMR (CDCl₃) δ 8.55 (1H, d, J=2.9 Hz), 7.97 (2H, d, J=8.2 Hz), 7.82 (1H, dd, J=2.9, 8.1 Hz), 7.38-7.20 (5H, m), 6.86 (2H, d, J=8.9 Hz), 5.36-5.25 (1H, m), 5.22-5.10 (2H, m), 1.49 (3H, d, J=6.9 Hz);
MS (ESI) m/z 429 (M+H)⁺, 427 (M−H)⁻.

Example 22

4-{(1S)-1-[(5-chloro-2-{[(5-chloropyridin-2-yl)(methyl)amino]methyl}benzoyl)amino]ethyl}benzoic Acid

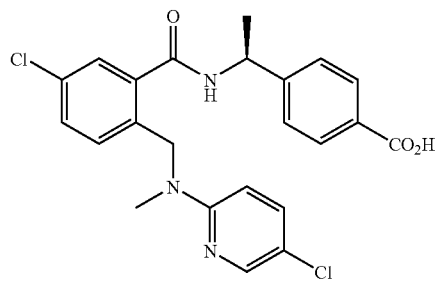

STEP 1. Methyl 5-chloro-2-{[(5-chloropyridin-2-yl)(methyl)amino]methyl}benzoate To s suspension of sodium hydride (60% dispersion in mineral oil, 46 mg, 1.1 mmol) in terahydorofuran (4 ml) was added 5-chloro-N-methylpyridin-2-amine (128 mg, 1.14 mmol) in tetrahydrofuran (5 ml) at room temperature and stirred for 30 min. The mixture was added methyl 2-(bromomethyl)-5-chlorobenzoate (250 mg, 0.95 mmol) in tetrahydrofuran (5 ml) at room temperature and stirred at 80° C. for 8 hr. After cooling to room temperature, the mixture was added water and extracted with ethyl acetate. The organic layer was dried over sodium sulfate and evaporated. The residue was purified by flush column chromatography on silica gel eluting with hexane/ethyl acetate (10/1) to afford 102 mg (33%) of the title compound:
¹H-NMR (CDCl₃) δ 8.07 (1H, d, J=2.6 Hz), 7.99 (1H, d, J=2.2 Hz), 7.42-7.33 (2H, m), 7.09 (1H, d, J=8.3 Hz), 6.83 (1H, d, J=9.0 Hz), 5.07 (2H, s), 3.91 (3H, s), 3.11 (3H, s).

STEP 2. 5-Chloro-2-{[(5-chloropyridin-2-yl)(methyl)amino]methyl}benzoic acid The title compound was prepared according to the procedure described in step 2 of Example 1 from methyl 5-chloro-2-{[(5-chloropyridin-2-yl)(methyl)amino]methyl}benzoate (step 1):
¹H-NMR (CDCl₃) δ 8.02-7.97 (1H, m), 7.93-7.89 (1H, m), 7.46 (1H, dd, J=2.6, 9.2 Hz), 7.38 (1H, d, J=2.4, 8.3 Hz), 7.18 (1H, d, J=8.3 Hz), 6.51 (1H, d, J=9.2 Hz), 4.98-4.89 (2H, br.s), 3.29 (3H, s).

STEP 3. Methyl 4-{(1S)-1-[(5-chloro-2-{[(5-chloropyridin-2-yl)(methyl)amino]methyl}benzoyl)amino]ethyl}benzoate The title compound was prepared according to the procedure described in step 6 of Example 1 from 5-chloro-2-{[(5-chloropyridin-2-yl)(methyl)amino]methyl}benzoic acid (step 2) and methyl 4-[(1S)-1-aminoethyl]benzoate hydrochloride (step 5 of Example 1):
¹H-NMR (CDCl₃) δ 8.19 (1H, d, J=7.8 Hz), 8.02 (2H, d, J=8.2 Hz), 7.72 (1H, d, J=2.6 Hz), 7.49 (1H, d, J=2.1 Hz), 7.45 (2H, d, J=8.2 Hz), 7.40 (1H, dd, J=2.6, 9.1 Hz), 7.27 (1H, dd, J=2.1, 8.2 Hz), 7.15 (1H, d, J=8.2 Hz), 6.48 (1H, d, J=9.1 Hz), 5.42-5.27 (1H, m), 4.82 (1H, d, J=16.3 Hz), 4.69 (1H, d, J=16.3 Hz), 3.92 (3H, s), 3.20 (3H, s), 1.60 (3H, d, J=6.9 Hz).

STEP 4. 4-{(1S)-1-[(5-Chloro-2-{[(5-chloropyridin-2-yl)(methyl)amino]methyl}benzoyl)amino]ethyl}benzoic acid The title compound was prepared according to the procedure described in step 7 of Example 1 from methyl 4-{(1S)-1-[(5-chloro-2-{[(5-chloropyridin-2-yl)(methyl)amino]methyl}benzoyl)amino]ethyl}benzoate (step 3):
¹H-NMR (CDCl₃) δ 8.23 (1H, d, J=7.6 Hz), 8.07 (2H, d, J=8.2 Hz), 7.74 (1H, d, J=2.2 Hz), 7.54-7.44 (3H, m), 7.41 (1H, dd, J=2.6, 9.1 Hz), 7.31-7.25 (1H, m), 7.15 (1H, d, J=8.4 Hz), 6.49 (1H, d, J=9.1 Hz), 5.43-5.30 (1H, m), 4.84 (1H, d, J=16.5 Hz), 4.71 (1H, d, J=16.5 Hz), 3.21 (3H, s), 1.61 (3H, d, J=6.9 Hz);
MS (ESI) m/z 458 (M+H)⁺, 456 (M−H)⁻.

Example 23

4-{(1S)-1-({5-chloro-2-[(cyclohexylmethoxy)methyl]benzoyl}amino)ethyl}benzoic Acid

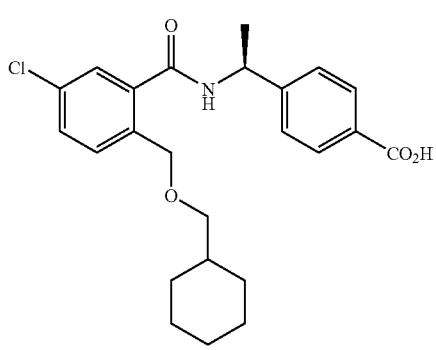

STEP 1. Methyl 4-[(1S)-1-({5-chloro-2-[(cyclohexylmethoxy)methyl]benzoyl}amino)ethyl]benzoate To a solution of potassium tert-butoxide (533 mg, 4.75 mmol) in tetrahydrofuran (10 ml) was added cyclohexylmethanol (594 mg, 5.20 mmol) in tetrahydrofuran (2.5 ml), methyl 2-(bromomethyl)-5-chlorobenzoate (250 mg, 0.95 mmol) in tetarahydrofuran (2.5 ml) at 0° C. The reaction mixture was stirred at room temperature for 2 hours. The resulting solution was acidified with 2 N hydrochloric acid solution (pH ca. 2) at 0° C. It was extracted with dichloromethane, the organic extracts were dried over sodium sulfate and concentrated to afford 302 mg of crude 5-chloro-2-[(cyclohexylmethoxy)methyl]benzoic acid. This carboxylic acid was converted into 132 mg (31%) of the title compound according to the procedure described in step 6 of Example 1:

$^1$H-NMR (CDCl$_3$) δ 8.13-8.03 (1H, m), 8.03 (2H, d, J=8.2 Hz), 7.81 (1H, d, J=2.2 Hz), 7.47 (2H, d, J=8.2 Hz), 7.38 (1H, dd, J=2.2, 8.1 Hz), 7.24 (1H, d, J=8.1 Hz), 5.48-5.29 (1H, m), 4.51 (1H, d, J=11.5 Hz), 4.44 (1H, d, J=11.5 Hz), 3.91 (3H, s), 3.26-3.10 (2H, m), 1.75-1.54 (6H, m), 1.59 (3H, d, J=7.1 Hz), 1.50-1.35 (1H, m), 1.23-1.05 (2H, m), 0.93-0.73 (2H, m).

STEP 2. 4-{(1S)-1-({5-Chloro-2-[(cyclohexylmethoxy)methyl]benzoyl}amino)ethyl}benzoic acid The title compound was prepared according to the procedure described in step 7 of Example 1 from methyl 4-[(1S)-1-({5-chloro-2-[(cyclohexylmethoxy)methyl]benzoyl}amino)ethyl]benzoate (step 1):

$^1$H-NMR (CDCl$_3$) δ 8.14 (1H, d, J=7.4 Hz), 8.09 (2H, d, J=8.2 Hz), 7.83 (1H, d, J=2.3 Hz), 7.50 (2H, d, J=8.2 Hz), 7.39 (1H, dd, J=2.3, 8.1 Hz), 7.25 (1H, d, J=8.1 Hz), 5.48-5.33 (1H, m), 4.53 (1H, d, J=11.5 Hz), 4.46 (1H, d, J=11.5 Hz), 3.29-3.12 (2H, m), 1.74-1.58 (6H, m), 1.61 (3H, d, J=6.9 Hz), 1.53-1.33 (1H, m), 1.26-1.08 (2H, m), 0.93-0.78 (2H, m);

MS (ESI) m/z 458 (M+H)$^+$, 456 (M−H)$^-$.

Example 24

4-{(1S)-1-({5-chloro-2-[(2,2-dimethylpropoxy)methyl]benzoyl}amino)ethyl}benzoic Acid

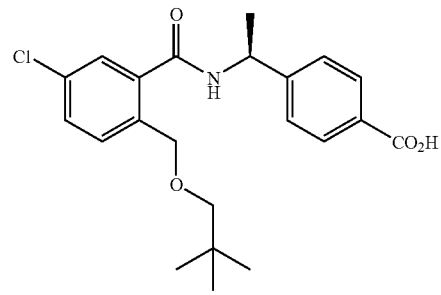

STEP 1. Methyl 4-[(1S)-1-({5-chloro-2-[(2,2-dimethylpropoxy)methyl]benzoyl}amino)ethyl]benzoate The title compound was prepared according to the procedure described in step 1 of Example 23 from methyl 2-(bromoethyl)-5-chlorobenzoate via 5-chloro-2-[(2,2-dimethylpropoxy)methyl]benzoic acid as an intermediate:

$^1$H-NMR (CDCl$_3$) δ 8.12-8.00 (1H, m), 8.03 (2H, d, J=8.4 Hz), 7.81 (1H, d, J=2.3 Hz), 7.48 (2H, d, J=8.4 Hz), 7.39 (1H, dd, J=2.3, 8.1 Hz), 7.26 (1H, d, J=8.1 Hz), 5.46-5.33 (1H, m), 4.53 (2H, s), 3.91 (3H, s), 3.10 (1H, d, J=8.6 Hz), 3.03 (1H, d, J=8.6 Hz), 1.59 (3H, d, J=7.1 Hz), 0.84 (9H, s).

STEP 2. 4-{(1S)-1-({5-Chloro-2-[(2,2-dimethylpropoxy)methyl]benzoyl}amino)ethyl}benzoic acid The title compound was prepared according to the procedure described in step 7 of Example 1 from methyl 4-[(1S)-1-({5-chloro-2-[(2,2-dimethylpropoxy)methyl]benzoyl}amino)ethyl]benzoate (step 1):

$^1$H-NMR (CDCl$_3$) δ 8.13-8.05 (3H, m), 7.84 (1H, d, J=2.2 Hz), 7.51 (2H, d, J=8.2 Hz), 7.40 (1H, dd, J=2.2, 8.1 Hz), 7.26 (1H, d, J=8.1 Hz), 5.49-5.34 (1H, m), 4.55 (2H, s), 3.11 (1H, d, J=8.6 Hz), 3.04 (1H, d, J=8.6 Hz), 1.61 (3H, d, J=6.9 Hz), 0.84 (9H, s);

MS (ESI) m/z 404 (M+H)$^+$, 402 (M−H)$^-$.

Example 25

4-{(1S)-1-[(5-chloro-2-{[(5-fuluoropyridin-2-yl)(methyl)amino]methyl}benzoyl)amino]ethyl}benzoic Acid

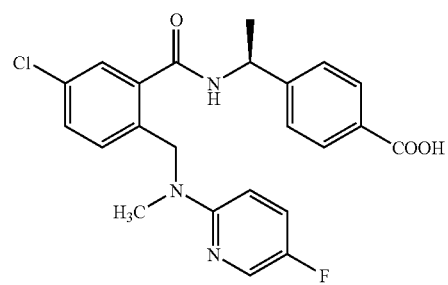

STEP 1. 5-Fluoro-N-methylpyridin-2-amine

To a suspension of sodium hydride (60% dispersion in mineral oil, 117.8 mg, 4.91 mmol) in tetrahydrofuran (25 ml) was added a solution of 5-fluoropyridin-2-amine (500 mg, 4.46 mmol) in tetrahydrofuran (25 ml) at room temperature and the reaction mixture was stirred at 40° C. for 30 min. Then to the reaction mixture was added methyl iodide (696.9 mg, 4.91 mmol) at −40° C. and the resulting mixture was stand at room temperature overnight with stirring. The reaction was quenched by the addition of water and whole mixture was extracted with ethyl acetate. The organic extracts were dried over sodium sulfate and concentrated. The residue was purified by flush column chromatography on silica gel eluting with hexane/ethyl acetate (4/1) to afford 129 mg (23%) of the title compound:

$^1$H-NMR (CDCl$_3$) δ 7.97 (1H, d, J=2.6 Hz), 7.28-7.17 (1H, m), 6.34 (1H, dd, J=3.5, 9.1 Hz), 2.90 (3H, d, J=5.1 Hz).

STEP 2. Methyl 5-chloro-2-{[(5-fluoropyridin-2-yl)(methyl)amino]methyl}benzoate The title compound was prepared according to the procedure described in step 1 of Example 22 from methyl 2-(bromoethyl)-5-chlorobenzoate and 5-fluoro-N-methylpyridin-2-amine (step 1):

$^1$H-NMR (CDCl$_3$) δ 8.00 (1H, d, J=3.3 Hz), 7.99 (1H, d, J=2.2 Hz), 7.39 (1H, dd, J=2.2, 8.4 Hz) 7.25-7.16 (1H, m), 7.13 (1H, d, J=8.4 Hz), 6.37 (1H, dd, J=3.3, 9.2 Hz), 5.05 (2H, s), 3.90 (3H, s), 3.11 (3H, s).

STEP 3. Methyl 4-{(1S)-1-[(5-chloro-2-{[(5-fluoropyridin-2-yl)(methyl)amino]methyl}benzoyl)amino]ethyl}benzoate The title compound was prepared according to the procedure described in step 2 and 6 of Example 1 from methyl 5-chloro-2-{[(5-fluoropyridin-2-yl)(methyl)amino]methyl}benzoate (step 2) via 5-chloro-2-{[(5-fluoropyridin-2-yl)(methyl)amino]methyl}benzoic acid as an intermediate:

$^1$H-NMR (CDCl$_3$) δ 8.32 (1H, d, J=7.3 Hz), 8.00 (2H, d, J=8.3 Hz), 7.71 (1H, d, J=2.9 Hz), 7.49 (1H, d, J=2.0 Hz), 7.43 (2H, d, J=8.3 Hz), 7.31-7.19 (2H, m), 7.16 (1H, d, J=8.3 Hz), 6.48 (1H, dd, J=3.3, 9.4 Hz), 5.43-5.25 (1H, m), 4.78 (1H, d, J=16.3 Hz), 4.67 (1H, d, J=16.3 Hz), 3.90 (3H, s), 3.17 (3H, s), 1.57 (3H, d, J=7.2 Hz).

STEP 4. 4-{(1S)-1-[(5-Chloro-2-{[(5-fluoropyridin-2-yl)(methyl)amino]methyl}benzoyl)amino]ethyl}benzoic acid The title compound was prepared according to the procedure described in step 7 of Example 1 from methyl 4-{(1S)-1-[(5-chloro-2-{[(5-fluoropyridin-2-yl)(methyl)amino]methyl}benzoyl)amino]ethyl}benzoate (step 3):

$^1$H-NMR (CDCl$_3$) δ 8.35 (1H, d, J=7.5 Hz), 8.06 (2H, d, J=8.3 Hz), 7.73 (1H, d, J=2.9 Hz), 7.52 (1H, d, J=2.2 Hz), 7.47 (2H, dd, J=8.3 Hz), 7.33-7.21 (2H, m), 7.18 (1H, d, J=8.3 Hz), 6.50 (1H, dd, J=3.3, 9.4 Hz), 5.42-5.32 (1H, m), 4.80 (1H, d, J=16.0 Hz), 4.69 (1H, d, J=16.0 Hz), 3.19 (3H, s), 1.59 (3H, d, J=7.2 Hz);

MS (ESI) m/z 442 (M+H)$^+$, 440 (M−H)$^−$.

Example 26

4-{(1S)-1-[({5-chloro-2-[(3-fluorophenoxy)methyl]pyridin-3-yl}carbonyl)amino]ethyl}benzoic Acid

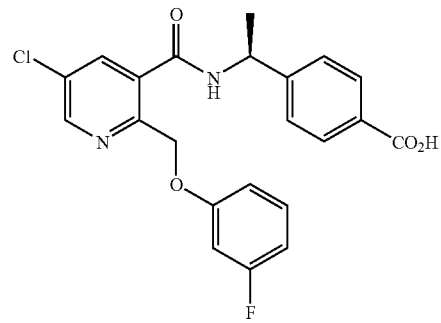

STEP 1. Ethyl 2,5-dichloronicotinate

To a solution of 2,5-dichloronicotinic acid (30 g, 0.16 mol) in toluene (100 ml) was added ethanol (50 ml) and conc. sulfuric acid (1 ml). The reaction mixture was heated at 130° C. for 3 days with stirring. Then the reaction mixture was cooled and poured into sat. sodium bicarbonate solution. The whole mixture was extracted with ethyl acetate. The organic phase was washed with brine, dried (sodium sulfate), and concentrated to afford 34 g (quant.) of title compound:

$^1$H-NMR (CDCl$_3$) δ 8.48 (1H, d, J=2.6 Hz), 8.15 (1H, d, J=2.6 Hz), 4.44 (2H, dd, J=7.1, 14.3 Hz), 1.42 (3H, t, J=7.1 Hz).

STEP 2. Ethyl 5-chloro-2-methylnicotinate

A mixture of ethyl 2,5-dichloronicotinate (step 1, 10 g, 0.045 mol), tetrakis(triphenylphoshine)palladium (5.2 g, 4.5 mmol), trimethylboroxine (5.65 g, 0.045 mmol) and potassium carbonate (18.66 g, 0.16 mmol) in 1,4-dioxane (contain 10% water, 100 ml) was refluxed for 7 h under nitrogen atmosphere. The reaction mixture was cooled to room temperature and poured into water. The aqueous mixture was extracted with ethyl acetate. The organic extracts were dried over sodium sulfate and concentrated. The residue was purified by flush column chromatography on silica gel eluting with hexane/ethyl acetate (50/1 to 20/1) to afford 3.41 g (38%) of the title compound:

$^1$H-NMR (CDCl$_3$) δ 8.57 (1H, d, J=2.5 Hz), 8.17 (1H, d, J=2.5 Hz), 4.39 (2H, dd, J=7.1, 14.2 Hz), 2.81 (3H, s), 1.41 (3H, t, J=7.1 Hz).

STEP 3. Ethyl 5-chloro-2-methylnicotinate 1-oxide

The title compound was prepared according to the procedure described in step 3 of Example 21 from ethyl 5-chloro-2-methylnicotinate (step 2):

$^1$H-NMR (CDCl$_3$) δ 8.50 (1H, d, J=1.8 Hz), 7.74 (1H, d, J=1.8 Hz), 4.42 (2H, dd, J=7.1, 14.2 Hz), 2.75 (3H, s), 1.41 (3H, t, J=7.1 Hz).

STEP 4. Ethyl 5-chloro-2-(hydroxymethyl)nicotinate

To a solution of ethyl 5-chloro-2-methylnicotinate 1-oxide (step 3, 4.1 g, 19 mmol) in dichloromethane (100 ml) was added trifluoromethane acetic acid anhydride (4 ml) at room temperature and the reaction mixture was stirred for 3 days. The reaction mixture was added 2 N hydrochloric acid solution (30 ml) with stirring. After 30 min, the whole mixture was extracted with dichloromethane. The organic phase was washed with water and brine, dried over sodium sulfate, and concentrated. The residue was purified by flush column chromatography on silica gel eluting with hexane/ethyl acetate (20/1 to 4/1) to afford 840 mg (20%) of the title compound:

$^1$H-NMR (CDCl$_3$) δ 8.69 (1H, d, J=2.3 Hz), 8.34 (1H, d, J=2.3 Hz), 5.06 (2H, s), 4.42 (2H, dd, J=7.1, 14.9 Hz), 1.42 (3H, t, J=7.1 Hz).

STEP 5. Ethyl 5-chloro-2-[(3-fluorophenoxy)methyl]nicotinate

To a mixture of ethyl 5-chloro-2-(hydroxymethyl)nicotinate (step 4, 340 mg, 1.59 mmol), 3-fluorophenol (325 mg, 2.90 mmol), and triphenylphosphine (761 mg, 2.9 mmol) in tetrahydrofuran (10 ml) was added 40% solution of diethylazodicarboxylate in toluene (506 mg, 2.9 mmol) and the reaction mixture was stirred at room temperature for 5 hours. To the reaction mixture was added water and the whole mixture was extracted with ethyl acetate. The organic phase was dried over sodium sulfate and evaporated. The residue was purified by flush column chromatography on silica gel eluting with hexane/ethyl acetate (4/1) to afford 300 mg (56%) of the title compound:

$^1$H-NMR (CDCl$_3$) δ 8.69 (1H, d, J=2.3 Hz), 8.23 (1H, d, J=2.3 Hz), 7.27-7.15 (1H, m), 6.80-6.63 (3H, m), 5.49 (2H, s), 4.37 (2H, dd, J=7.1, 14.2 Hz), 1.33 (3H, t, J=7.1 Hz).

STEP 6. 5-Chloro-2-[(3-fluorophenoxy)methyl]nicotinic acid

The title compound was prepared according to the procedure described in step 7 of Example 1 from ethyl 5-chloro-2-[(3-fluorophenoxy)methyl]nicotinate (step 5):

MS (ESI) m/z 282 (M+H)$^+$, 280 (M−H)$^-$.

STEP 7. Methyl 4-{(1S)-1-[({5-chloro-2-[(3-fluorophenoxy)methyl]pyridin-3-yl}carbonyl)amino]ethyl}benzoate The title compound was prepared according to the procedure described in step 6 of Example 1 from 5-chloro-2-[(3-fluorophenoxy)methyl]nicotinic acid (step 6) and methyl 4-[(1S)-1-aminoethyl]benzoate hydrochloride (step 5 of Example 1):

$^1$H-NMR (CDCl$_3$) δ 8.62 (1H, d, J=2.4 Hz), 8.00 (1H, d, J=2.4 Hz), 7.89 (2H, d, J=8.3 Hz), 7.34-7.14 (4H, m), 6.76-6.65 (2H, m), 6.65-6.56 (1H, m), 5.34-5.20 (1H, m), 5.17 (1H, d, J=10.5 Hz), 5.12 (1H, d, J=10.5 Hz), 3.91 (3H, s), 1.47 (3H, d, J=7.0 Hz).

STEP 8. 4-{(1S)-1-[({5-chloro-2-[(3-fluorophenoxy)methyl]pyridin-3-yl}carbonyl)amino]ethyl}benzoic acid The title compound was prepared according to the procedure described in step 7 of Example 1 from methyl 4-{(1S)-1-[({5-chloro-2-[(3-fluorophenoxy)methyl]pyridin-3-yl}carbonyl)amino]ethyl}benzoate (step 7):

$^1$H-NMR (DMSO-d$_6$) 69.19 (1H, d, J=7.7 Hz), 8.73 (1H, d, J=2.2 Hz), 8.10 (1H, d, J=2.2 Hz), 7.84 (2H, d, J=8.3 Hz), 7.47 (2H, d, J=8.3 Hz), 7.25 (1H, dd, J=8.1, 15.8 Hz), 6.83-6.60 (3H, m), 5.24 (1H, d, J=11.6 Hz), 5.18 (1H, d, J=11.6 Hz), 5.16-5.03 (1H, m), 1.4.1 (3H, d, J=7.0 Hz); MS (ESI) m/z 429 (M+H)$^+$, 427 (M−H)$^-$.

Example 27

4-{(1S)-1-[({5-chloro-2-[(4-fluorophenoxy)methyl]pyridin-3-yl}carbonyl)amino]ethyl}benzoic Acid

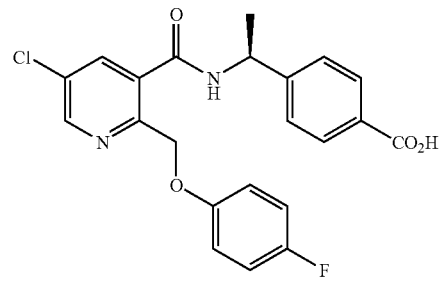

STEP 1. 5-Chloro-2-[(4-fluorophenoxy)methyl]nicotinic acid

The title compound was prepared according to the procedure described in step 2 of Example 18 from 3-chlorofuro[3,4-b]pyridin-5 (7H)-one (step 1 of Example 18) and 4-fluorophenol:

$^1$H-NMR (CDCl$_3$) δ 8.73-8.62 (1H, brs), 8.30-8.19 (1H, brs), 6.98-6.80 (4H, m), 5.47 (2H, s).

STEP 2. Methyl-4-{(1S)-1-[({5-chloro-2-[(4-fluorophenoxy)methyl]pyridin-3-yl}carbonyl)amino]ethyl}benzoate The title compound was prepared according to the procedure described in step 6 of Example 1 from 5-chloro-2-[(4-fluorophenoxy)methyl]nicotinic acid (step 1) and methyl 4-[(1S)-1-aminoethyl]benzoate hydrochloride (step 5 of Example 1):

$^1$H-NMR (CDCl$_3$) δ 8.62 (1H, d, J=2.4 Hz), 8.05 (1H, d, J=2.4 Hz), 7.89 (2H, d, J=8.4 Hz), 7.34-7.27 (3H, m), 7.02-6.91 (2H, m), 6.87-6.78 (2H, m), 5.34-5.22 (1H, m), 5.14 (1H, d, J=10.1 Hz), 5.10 (1H, d, J=10.1 Hz), 3.92 (3H, s), 1.47 (3H, d, J=7.0 Hz).

STEP 3. 4-{(1S)-1-[({5-Chloro-2-[(4-fluorophenoxy)methyl]pyridin-3-yl}carbonyl) amino]ethyl}benzoic acid The title compound was prepared according to the procedure described in step 7 of Example 1 from methyl 4-{(1S)-1-[({5-chloro-2-[(4-fluorophenoxy)methyl]pyridin-3-yl}carbonyl)amino]ethyl}benzoate (step 2):

$^1$H-NMR (CDCl$_3$) δ 8.63 (1H, d, J=2.4 Hz), 8.07 (1H, d, J=2.4 Hz), 7.97 (2H, d, J=8.3 Hz), 7.40-7.28 (3H, m), 7.03-6.94 (2H, m), 6.92-6.83 (2H, m), 5.37-5.24 (1H, m), 5.17 (1H, d, J=10.3 Hz), 5.12 (1H, d, J=10.3 Hz), 1.48 (3H, d, J=7.0 Hz); MS (ESI) m/z 429 (M+H)$^+$, 427 (M−H)$^-$.

Experimental Example cAMP assay in human EP$_4$ transfectant were conducted using the method described above. The results of these studies are summarized in Table 1.

TABLE 1

Results of cAMP assay in human EP$_4$ transfectant

| Compound | cAMP IC50 (nM) |
|---|---|
| EXAMPLE 1; 4-[(1S)-1-({5-Chloro-2-[(2-chlorophenoxy)methyl]benzoyl}amino)ethyl]benzoic acid | 19 |
| EXAMPLE 2; 4-[(1S)-1-({5-Chloro-2-[(3-chlorophenoxy)methyl]benzoyl}amino)ethyl]benzoic acid | 11 |
| EXAMPLE 3; 4-[(1S)-1-({5-Chloro-2-[(4-chlorophenoxy)methyl]benzoyl}amino)ethyl]benzoic acid | 7.5 |
| EXAMPLE 4; 4-[(1S)-1-({5-Chloro-2-[(4-fluorophenoxy)methyl]benzoyl}amino)ethyl]benzoic acid | 15 |
| EXAMPLE 5; 4-[(1S)-1-({5-Chloro-2-[(3-fluorophenoxy)methyl]benzoyl}amino)ethyl]benzoic acid | 23 |
| EXAMPLE 6; 4-[(1S)-1-({5-Chloro-2-[(2-fluorophenoxy)methyl]benzoyl}amino)ethyl]benzoic acid | 30 |
| EXAMPLE 7; 4-[(1S)-1-({5-Chloro-2-[(2,3-difluorophenoxy)methyl]benzoyl}amino)ethyl]benzoic acid | 15 |
| EXAMPLE 8; 4-[(1S)-1-({5-Chloro-2-[(2,4-difluorophenoxy)methyl]benzoyl}amino)ethyl]benzoic acid | 17 |
| EXAMPLE 9; 4-[(1S)-1-({5-Chloro-2-[(2,5-difluorophenoxy)methyl]benzoyl}amino)ethyl]benzoic acid | 41 |
| EXAMPLE 10; 4-[(1S)-1-({5-Chloro-2-[(2,6-difluorophenoxy)methyl]benzoyl}amino)ethyl]benzoic acid | 24 |
| EXAMPLE 11; 4-[(1S)-1-({5-Chloro-2-[(3,4-difluorophenoxy)methyl]benzoyl}amino)ethyl]benzoic acid | 16 |
| EXAMPLE 12; 4-[(1S)-1-({5-Chloro-2-[(3,5-difluorophenoxy)methyl]benzoyl}amino)ethyl]benzoic acid | 22 |
| EXAMPLE 13; 4-[(1S)-1-({5-Chloro-2-[(4-methylphenoxy)methyl]benzoyl}amino)ethyl]benzoic acid | 8.3 |
| EXAMPLE 14; 4-{(1S)-1-[(5-Chloro-2-{[(5-fluoropyridin-3-yl)oxy]methyl}benzoyl)amino]ethyl}benzoic acid | 380 |
| EXAMPLE 15; 4-{(1S)-1-[(5-Chloro-2-{[(5-chloropyridin-3-yl)oxy]methyl}benzoyl)amino]ethyl}benzoic acid | 160 |
| EXAMPLE 16; 4-[(1S)-1-({5-Chloro-2-[(cyclopentyloxy)methyl]benzoyl}amino)ethyl]benzoic acid | 470 |
| EXAMPLE 17; 4-((1S)-1-{[5-Chloro-2-(isobutoxymethyl)benzoyl]amino}ethyl)benzoic acid | 180 |
| EXAMPLE 18; 4-{(1S)-1-[({5-Chloro-2-[(4-chlorophenoxy)methyl]pyridin-3-yl}carbonyl)amino]ethyl}benzoic acid | 22 |
| EXAMPLE 19; 4-((1S)-1-{[5-Chloro-2-({3-[(methylamino)carbonyl]phenoxy}methyl)benzoyl]amino}ethyl)benzoic acid | 220 |
| EXAMPLE 20; 4-{(1S)-1-[({5-Chloro-2-[(3-chlorophenoxy)methyl]pyridin-3-yl}carbonyl)amino]ethyl}benzoic acid | 17 |
| EXAMPLE 21; 4-{(1S)-1-[({2-[(4-Chlorophenoxy)methyl]-5-fluoropyridin-3-yl}carbonyl)amino]ethyl}benzoic acid | 48 |
| EXAMPLE 22; 4-{(1S)-1-[(5-Chloro-2-{[(5-chloropyridin-2-yl)(methyl)amino]methyl}benzoyl)amino]ethyl}benzoic acid | 68 |
| EXAMPLE 23; 4-{(1S)-1-({5-Chloro-2-[(cyclohexylmethoxy)methyl]benzoyl}amino)ethyl}benzoic acid | 10 |
| EXAMPLE 24; 4-{(1S)-1-({5-Chloro-2-[(2,2-dimethylpropoxy)methyl]benzoyl}amino)ethyl}benzoic acid | 120 |
| EXAMPLE 25; 4-{(1S)-1-[(5-Chloro-2-{[(5-fluoropyridin-2-yl)(methyl)amino]methyl}benzoyl)amino]ethyl}benzoic acid | 230 |
| EXAMPLE 26; 4-{(1S)-1-[({5-Chloro-2-[(3-fluorophenoxy)methyl]pyridin-3-yl}carbonyl)amino]ethyl}benzoic acid | 56 |
| EXAMPLE 27; 4-{(1S)-1-[({5-Chloro-2-[(4-fluorophenoxy)methyl]pyridin-3-yl}carbonyl)amino]ethyl}benzoic acid | 91 |

IC50: the concentration of the individual compound required to reduce the amount of ligand by 50%.

What is claimed is:

1. A compound of the formula (I):

(I)

wherein
X represents —CH—;
Y represents —NR$^4$, an oxygen atom or a sulfur atom;
R$^4$ represents a hydrogen atom or an alkyl group having from 1 to 3 carbon atoms;
Z represents a hydrogen atom or a halogen atom;
R$^1$ represents an alkyl group having from 1 to 6 carbon atoms optionally substituted with an alkoxy group having from 1 to 6 carbon atoms or a cycloalkyl group having from 3 to 7 carbon atoms; a cycloalkyl group having from 3 to 7 carbon atoms optionally substituted by an alkyl group having from 1 to 3 carbon atoms; or a phenyl group optionally substituted with one or more substituents α;
R$^2$ and R$^3$ independently represent a hydrogen atom or an alkyl group having from 1 to 3 carbon atoms; or R$^2$ and R$^3$ groups together form an alkylene chain having from 3 to 6 carbon atoms; and
said substituent α is selected from the group consisting of halogen atoms, alkyl groups having from 1 to 4 carbon atoms, haloalkyl groups having from 1 to 4 carbon atoms, hydroxy groups, alkoxy groups having from 1 to 4 carbon atoms, haloalkoxy groups having from 1 to 4 carbon atoms, cyano groups, hydroxy alkyl groups having from 1 to 4 carbon atoms, alkoxyalkyl groups having from 1 to 4 carbon atoms in alkoxy and alky groups, alkylsulfonyl groups having from 1 to 4 carbon atoms, alkanoyl groups having from 2 to 5 carbon atoms, alkenyl groups having from 2 to 4 carbon atoms, alkynyl groups having from 2 to 4 carbon atoms, alkylthio groups having from 1 to 4 carbon atoms, nitro groups, amino groups, mono- or di-alkylamino groups having from 1 to 4 carbon atoms, aminosulfonyl groups, alkoxycarbonyl groups having from 1 to 4 carbon atoms, alkylsufonylamino groups having from 1 to 4 carbon atoms, cycloalkyl groups having from 3 to 7 carbon atoms and a mono- or di-alkylaminocarbonyl groups having from 1 to 6 carbon atoms;
or a pharmaceutically acceptable ester of such compound;
or a pharmaceutically acceptable salt thereof.

2. A compound according to claim 1, wherein
Y represents $NR^4$ or an oxygen atom; and
$R^4$ represents an alkyl group having from 1 to 3 carbon atoms.

3. A compound according to claim 1, wherein
Y represents an oxygen atom.

4. A compound according to claim 1, wherein
Z represents a halogen atom.

5. A compound according to claim 1, wherein
$R^1$ represents an alkyl group having from 1 to 6 carbon atoms;
a cycloalkyl group having from 3 to 7 carbon atoms, a phenyl group optionally substituted with one or more substituents α;
said substituents α are selected from the group consisting of halogen atoms, alkyl groups having from 1 to 4 carbon atoms, haloalkyl groups having from 1 to 4 carbon atoms, hydroxy groups, alkoxy groups having from 1 to 4 carbon atoms, haloalkoxy groups having from 1 to 4 carbon atoms, cyano groups, hydroxy alkyl groups having from 1 to 4 carbon atoms, alkoxyalkyl groups having from 1 to 4 carbon atoms in alkoxy and alky groups, alkylsulfonyl groups having from 1 to 4 carbon atoms and alkanoyl groups having from 2 to 5 carbon atoms.

6. A compound according to claim 1, wherein
$R^1$ represents an alkyl group having from 1 to 6 carbon atoms, a cycloalkyl group having from 4 to 6 carbon atom, or a phenyl group referred to in the definitions of $R^1$ is unsubstituted or is substituted by at least one substituent selected from the group consisting of substituents α; and
said substituents α are selected from the group consisting of halogen atoms, alkyl groups having from 1 to 2 carbon atoms and cyano groups.

7. A compound according to claim 1, wherein
$R^1$ represents a phenyl group, optionally substituted by 1 to 2 groups independently selected from a fluorine atom, a chlorine atom and a methyl group.

8. A compound according to claim 1, wherein
$R^2$ and $R^3$ independently represent a hydrogen atom or an alkyl group having from 1 to 3 carbon atoms.

9. A compound according to claim 1, wherein
$R^2$ represents a hydrogen atom; and $R^3$ represents a methyl group.

10. A compound according to claim 1 selected from:
4-[(1S)-1-({5-Chloro-2-[(4-chlorophenoxy)methyl]benzoyl}amino)ethyl]benzoic acid;
4-[(1S)-1-({5-Chloro-2-[(4-methylphenoxy)methyl]benzoyl}amino)ethyl]benzoic acid;
4-[(1S)-1-({5-Chloro-2-[(3-chlorophenoxy)methyl]benzoyl}amino)ethyl]benzoic acid;
4-[(1S)-1-({5-Chloro-2-[(4-fluorophenoxy)methyl]benzoyl}amino)ethyl]benzoic acid;
4-[(1S)-1-({5-Chloro-2-[(2,3-difluorophenoxy)methyl]benzoyl}amino)ethyl]benzoic acid;
4-[(1S)-1-({5-Chloro-2-[(3,4-difluorophenoxy)methyl]benzoyl}amino)ethyl]benzoic acid;
4-[(1S)-1-({5-Chloro-2-[(2,4-difluorophenoxy)methyl]benzoyl}amino)ethyl]benzoic acid;
4-{(1S)-1-[({5-Chloro-2-[(3-chlorophenoxy)methyl]pyridin-3-yl}carbonyl)amino]ethyl}benzoic acid;
4-[(1S)-1-({5-Chloro-2-[(2-chlorophenoxy)methyl]benzoyl}amino)ethyl]benzoic acid;
4-[(1S)-1-({5-Chloro-2-[(3,5-difluorophenoxy)methyl]benzoyl}amino)ethyl]benzoic acid;
4-[(1S)-1-({5-Chloro-2-[(3-fluorophenoxy)methyl]benzoyl}amino)ethyl]benzoic acid;
4-[(1S)-1-({5-Chloro-2-[(2,6-difluorophenoxy)methyl]benzoyl}amino)ethyl]benzoic acid;
4-[(1S)-1-({5-Chloro-2-[(2-fluorophenoxy)methyl]benzoyl}amino)ethyl]benzoic acid;
4-[(1S)-1-({5-Chloro-2-[(2,5-difluorophenoxy)methyl]benzoyl}amino)ethyl]benzoic acid; and
or a pharmaceutically acceptable ester of such compound;
or a pharmaceutically acceptable salt thereof.

11. A pharmaceutical composition, which comprises a compound according to claim 1, or a pharmaceutically acceptable ester of such compound, or a pharmaceutically acceptable salt thereof, and a suitable pharmaceutically acceptable carrier.

12. A combination of a compound of the formula (I), as defined in claim 1, and another pharmacologically active agent.

* * * * *